United States Patent

Burton et al.

Patent Number: 5,064,649
Date of Patent: Nov. 12, 1991

[54] CEPHALOSPORIN DERIVATIVES

[75] Inventors: George Burton; Stephen C. M. Fell; John H. Bateson, all of Brockham Park, England

[73] Assignee: Beecham Group p.l.c., England

[21] Appl. No.: 407,231

[22] Filed: Sep. 14, 1989

[30] Foreign Application Priority Data

Sep. 16, 1988 [GB] United Kingdom ............... 8821797

[51] Int. Cl.⁵ .................. C07D 501/24; A61K 31/545
[52] U.S. Cl. ..................................... 424/114; 540/221; 540/222; 514/201; 514/202
[58] Field of Search ............... 540/222, 221; 514/202, 514/201; 424/114

[56] References Cited

U.S. PATENT DOCUMENTS 4,870,168  9/1989  Baker et al. ..................... 540/222

OTHER PUBLICATIONS

Chemical Abstracts, vol. 113, 114942h (1990).

Primary Examiner—Nicholas S. Rizzo
Attorney, Agent, or Firm—Rosenman & Colin

[57] ABSTRACT

β-Lactam antibiotics of the formula (Ia) or a pharmaceutically acceptable salt or pharmaceutically acceptable in vivo hydrolysable ester thereof are disclosed:

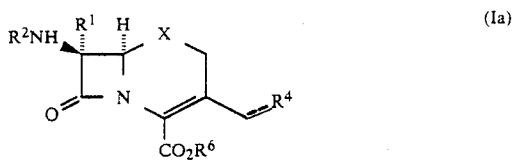

wherein $R^1$ is hydrogen, methoxy or formamido; $R^2$ is a acyl group, in particular that of an antibacterially active cephalosporin; $CO_2R^6$ is carboxy group or a carboxylate anion; $R^4$ is a butenolide or butanolide ring, optionally substituted by one or two alkyl, dialkylamino, alkoxy, hydroxy or aryl groups, which may be the same or different, or, wherein two adjacent carbon atoms which are available for substitution define the common bond of an aromatic fused bicyclic system; X is S, SO, $SO_2$, O or $CH_2$; and the dashed line adjacent to $R^4$ represents an optional double bond. Processes for the preparation of compounds together with intermediates for use therein are disclosed.

21 Claims, No Drawings

CEPHALOSPORIN DERIVATIVES

This invention relates to novel β-lactam containing compounds, their preparation and their use, and in particular to a novel class of cephalosporins. These compounds have antibacterial properties, and therefore are of use in the treatment of bacterial infections in humans and animals caused by a wide range of organisms.

We have now found a particular class of cephalosporins that possesses high antibacterial activity, in particular against Gram-positive organisms, and also shows good parenteral and oral absorption.

The present invention provides a compound of formula (I) or a salt thereof:

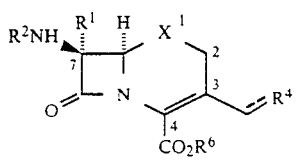

wherein $R^1$ is hydrogen, methoxy or formamido;

$R^2$ is an acyl group, in particular that of an antibacterially active cephalosporin;

$CO_2R^3$ is a carboxy group or a carboxylate anion, or $R^3$ is a readily removable carboxy protecting group (such as a pharmaceutically acceptable in-vivo hydrolysable ester group), $R^4$ is a butenolide or butanolide ring, optionally substituted by one or two alkyl, dialkylamino, alkoxy, hydroxy, halogen or aryl groups, which may be the same or different, or, wherein two adjacent carbon atoms which are available for substitution define the common bond of an aromatic fused bicyclic system; X is S,SO,-SO$_2$,O or CH$_2$; and the dashed line adjacent to $R^4$ represents an optional double bond.

When the optional double bond represented by the dashed line in formula (I) is absent, the carbon atom of $R^4$ to which it is bonded may be asymmetric. The present invention includes either stereoisomer, as well as mixtures of both isomers.

In compounds of formula (I) wherein $R^1$ is formamido, the formamido group can exist in conformations wherein the hydrogen atoms of the —NH—CHO moiety are cis- or trans-; of these the cis conformation normally predominates.

The terms butenolide and butanolide refer to dihydro- and tetrahydro-2-oxo-furan rings bonded via the 3-, 4- or 5-position carbon atom and optionally substituted at ring positions C-4 and C-5, C-3 and C-5, and C-3 and C-4 respectively. It will of course be appreciated that a C-4-linked ring, since there are no adjacent carbon atoms available for substitution, cannot form an aromatic fused bicyclic system.

Since the β-lactam antibiotic compounds of the present invention are intended for use as therapeutic agents in pharmaceutical compositions, it will be readily appreciated that preferred compounds within formula (I) are pharmaceutically acceptable, i.e. are compounds of formula (Ia) or pharmaceutically acceptable salts or pharmaceutically acceptable in vivo hydrolysable esters thereof:

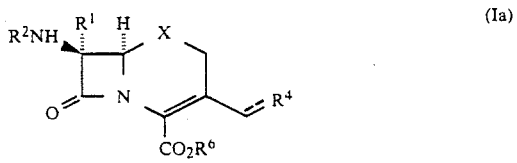

wherein $R^1$, $R^2$, $R^4$, X and the dashed line adjacent to $R^4$ are as defined with respect to formula (I) and the group $CO_2R^6$ is $CO_2R^3$ where $CO_2R^3$ is a carboxy group or a carboxylate anion.

Those compounds of the formula (I) wherein $R^3$ is a readily removable carboxy protecting group other than a pharmaceutically acceptable in vivo hydrolysable ester or which are in non-pharmaceutically acceptable salt form are primarily useful as intermediates in the preparation of compounds of the formula (Ia) or a pharmaceutically acceptable salt or pharmaceutically acceptable in vivo hydrolysable ester thereof.

Suitable readily removable carboxy protecting groups for the group $R^3$ include groups forming ester derivatives of the carboxylic acid, including in vivo hydrolysable esters. The derivative is preferably one which may readily be cleaved in vivo.

It will be appreciated that also included within the scope of the invention are salts and carboxy-protected derivatives, including in vivo hydrolysable esters, of any carboxy groups that may be present as optional substituents in compounds of formula (I) or (Ia). Also included within the scope of the invention are acid addition salts of any amino group or substituted amino group that may be present as optional substituents in compounds of formula (I) or (Ia).

Suitable ester-forming carboxyl-protecting groups are those which may be removed under conventional conditions. Such groups for $R^3$ include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl, stannyl or phosphorus-containing group, an oxime radical of formula —N=CHR$^7$ where $R^7$ is aryl or heterocyclic, or an in vivo hydrolysable ester radical such as defined below.

When used herein the term 'aryl' includes phenyl and naphthyl, each optionally substituted with up to five, preferably up to three, groups selected from halogen, mercapto, $C_{1-6}$ alkyl, phenyl, $C_{1-6}$ alkoxy, hydroxy($C_{1-6}$)alkyl, mercapto($C_{1-6}$)alkyl, halo($C_{1-6}$) alkyl, hydroxy, amino, nitro, carboxy, $C_{1-6}$ alkylcarbonyloxy, alkoxycarbonyl, formyl, or $C_{1-6}$ alkylcarbonyl groups.

The terms 'heterocyclyl' and 'heterocyclic' as used herein include aromatic and non-aromatic, single and fused, rings suitably containing up to four hetero-atoms in each ring selected from oxygen, nitrogen and sulphur, which rings may be unsubstituted or substituted by, for example, up to three groups selected from halogen, ($C_{1-6}$)alkyl, ($C_{1-6}$)alkoxy, halo($C_{1-6}$)alkyl, hydroxy, carboxy, carboxy salts, carboxy esters such as ($C_{1-6}$)alkoxycarbonyl, ($C_{1-6}$)alkoxycarbonyl($C_{1-6}$)alkyl, aryl, and oxo groups. Each heterocyclic ring suitably has from 4 to 7, preferably 5 or 6, ring atoms. A fused heterocyclic ring system may include carbocyclic rings and need include only one heterocyclic ring.

Compounds within the invention containing a heterocyclyl group may occur in two or more tautometric forms depending on the nature of the heterocyclyl group; all such tautomeric forms are included within the scope of the invention.

When used herein the terms 'alkyl' and 'alkoxy' (or 'lower alkyl' and 'lower alkoxy') include straight and branched chain alkyl groups containing from 1 to 6 carbon atoms, such as methyl, ethyl, propyl and butyl. A particular alkyl group is methyl.

When used herein the term 'halogen' refers to fluorine, chlorine, bromine and iodine.

A carboxyl group may be regenerated from any of the above esters by usual methods appropriate to the particular $R^3$ group, for example, acid- and base-catalysed hydrolysis, or by enzymically-catalysed hydrolysis, or by hydrogenolysis under conditions wherein the remainder of the molecule is substantially unaffected.

Examples of suitable pharmaceutically acceptable in vivo hydrolysable ester groups include those which break down readily in the human body to leave the parent acid or its salt. Suitable ester groups of this type include those of part formulae (i), (ii), (iii) and (iv):

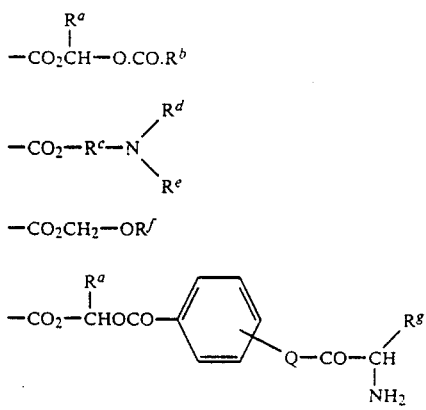

wherein $R^a$ is hydrogen, $C_{1-6}$ alkyl, $C_{3-7}$ cycloalkyl, methyl, or phenyl, $R^b$ is $C_{1-6}$ alkyl, $C_{1-6}$ alkoxy, phenyl, benzyl, $C_{3-7}$ cycloalkyl, $C_{1-6}$ alkyl $C_{3-7}$ cycloalkyl, 1-amino $C_{1-6}$ alkyl, or 1-($C_{1-6}$ alkyl)amino $C_{1-6}$ alkyl; or $R^a$ and $R^b$ together form a 1,2-phenylene group optionally substituted by one or two methoxy groups; $R^c$ represents $C_{1-6}$ alkylene optionally substituted with a methyl or ethyl group and $R^d$ and $R^e$ independently represent $C_{-6}$ alkyl; $R^f$ represents $C_{1-6}$ alkyl; $R^g$ represents hydrogen or phenyl optionally substituted by up to three groups selected from halogen, $C_{1-6}$ alkyl, or $C_{1-6}$ alkoxy; and Q is oxygen or NH.

Examples of suitable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl and α-ethoxycarbonyloxyethyl; dialkylaminoalkyl especially di-loweralkylamino alkyl groups such as dimethylaminomethyl, dimethylaminoethyl, diethylaminomethyl or diethylaminoethyl; lactone groups such as phthalidyl and dimethoxyphthalidyl; and esters linked to a second β-lactam antibiotic or to a β-lactamase inhibitor.

A further suitable pharmaceutically acceptable in vivo hydrolysable ester group is that of the formula:

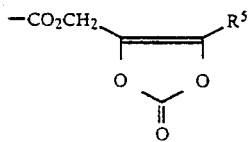

wherein $R^5$ is hydrogen, $C_{1-6}$ alkyl or phenyl. Suitable pharmaceutically acceptable salts of the carboxy group of the compound of formula (I) include metal salts, eg aluminium, alkali metal salts such as sodium or potassium, alkaline earth metal salts such as calcium or magnesium, and ammonium or substituted ammonium salts, for example those with lower alkylamines such as triethylamine, hydroxy-lower alkylamines such as 2-hydroxyethylamine, bis-(2-hydroxyethyl)amine or tris-(2-hydroxyethyl)amine, cycloalkylamines such as dicyclohexylamine, or with procaine, dibenzylamine, N,N-dibenzylethylenediamine, 1-ephenamine, N-methylmorpholine, N-ethylpiperidine, N-benzyl-β-phenethylamine, dehydroabietylamine, N,N'-bisdehydro-abietylamine, ethylenediamine, or bases of the pyridine type such as pyridine, collidine or quinoline, or other amines which have been used to form salts with known penicillins and cephalosporins. Other useful salts include the lithium salt and silver salt. Salts within compounds of formula (I), may be prepared by salt exchange in conventional manner.

In compounds of formula (I) or (Ia), the group X may be sulphur or an oxidised sulphur atom, i.e. a sulphoxide (SO) or sulphone ($SO_2$) group. When X is a sulphoxide group it will be understood that α- and β-isomers may exist; both such isomers are encompassed within the scope of the present invention.

Preferably X is sulphur.

Advantageously, $R^1$ is hydrogen. Suitable acyl groups $R^2$ include those of formulae (a)–(f):

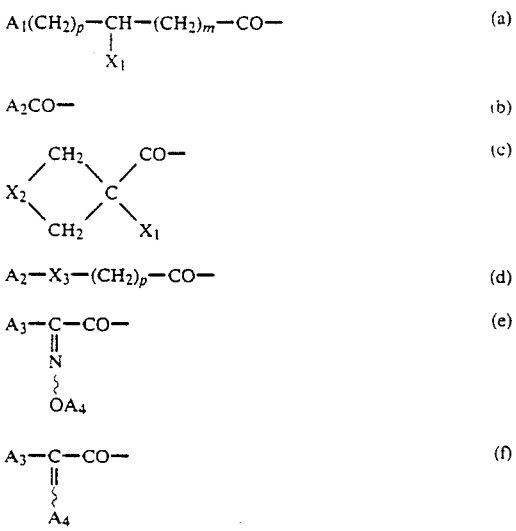

wherein p is 0, 1 or 2; m is 0, 1 or 2; $A_1$ is $C_{1-6}$ alkyl, substituted $C_{1-6}$ alkyl, $C_{3-6}$ cycloalkyl, cyclohexenyl, cyclohexadienyl, an aromatic (including heteroaromatic) group, such as phenyl, substituted phenyl, thienyl, pyridyl, or an optionally substituted thiazolyl group, a $C_{1-6}$ alkylthio group or $C_{1-6}$ alkyloxy; $X_1$ is a hydrogen or halogen atom, a carboxylic acid, carboxylic ester, sulphonic acid, azido, tetrazolyl, hydroxy, acyloxy, amino, ureido, acylamino, heterocyclylamino, guanidino or acylureido group; $A_2$ is an aromatic group, for example a phenyl, 2,6-dimethoxyphenyl,2-alkoxy-1-naphthyl, 3-arylisoxazolyl, or a 3-aryl-5-methylisoxazolyl group, such as 3-(2-chloro-6-fluorophenyl)-5-methylisoxazol-4-yl; a substituted alkyl group; or a substituted dithietane; $X_2$ is a —CH$_2$OCH$_2$—, —CH$_2$SCH$_2$—or alkylene group; $X_3$ is an oxygen or sulphur atom; $A_3$ is an aryl or heteroaryl group such as phenyl, substituted phenyl or aminothiazolyl in which the amino group is optionally protected; and $A_4$ is hydrogen, $C_{1-6}$ alkyl, $C_{3-8}$ cycloalkyl, $C_{1-6}$ alkoxycarbonyl($C_{1-6}$) alkyl, $C_{2-6}$ alkenyl, carboxy($C_{1-6}$)alkyl, $C_{2-6}$ alkynyl, aryl or aryl($C_{1-6}$)alkyl.

The term 'heteroaryl' as used herein means a heteroaromatic heterocyclic ring or ring system, suitably having 5 or 6 ring atoms in each ring.

Suitably when $R^2$ is a group (a), $A_1$ is $C_{1-6}$ alkyl, $C_{3-6}$ cycloalkyl, cyclohexenyl, cyclohexadienyl, phenyl, substituted phenyl such as hydroxyphenyl, thienyl or pyridyl; and $X_1$ is a hydrogen or halogen atom, or a carboxy, carboxylic ester, azido, tetrazolyl, hydroxy, acyloxy, optionally protected amino, ureido, guanidino or acylureido group.

Alternatively when $R^2$ is a group of formula (e), suitable values for the group $A_3$ include those commonly found in antibacterially active cephalosporins containing a hydroxyimino or substituted hydroxyimino group in the side chain attached to position 7 of the cephalosporin nucleus, for example phenyl, thien-2-yl, thien-3-yl, fur-2-yl, fur-3-yl, pyrid-2-yl, pyrid-3-yl, pyrid-4-yl, and 2-aminothiazol-4-yl in which the amino group is optionally protected.

Preferred groups for A3 include phenyl, 2-aminothiazol-4-yl, fur-2-yl, thien-2-yl, 2-(2-chloroacetamido)-thiazol-4-yl, 2-tritylaminothiazol-4-yl, 5-amino-1,2,4-thiadiazol-3-yl and 4-aminopyrimid-2-yl.

In compounds of formula (Ia), a particularly preferred group for A3 is 2-aminothiazol-4-yl.

Suitable values for the group $A_4$ include hydrogen, methyl, ethyl, cyclopropylmethyl, triphenylmethyl (trityl), cyclobutyl, cyclopentyl, cyclohexyl cycloheptyl, cyclooctyl, phenyl, carboxymethyl, carboxypropyl and t-butoxycarbonylmethyl.

Preferred values for $A_4$ in compounds of formula (Ia) include methyl and hydrogen.

It will be appreciated that compounds of the invention wherein $R^2$ is a group of formula (e) (or (f)) can exist as syn and anti (or E and Z) isomers or mixtures thereof. Both isomers are encompassed within the scope of this invention.

Preferably the compounds of the invention wherein $R^2$ is a group of formula (e) have the syn configuration (i.e. have the group $OA_4$ syn to the amide linkage) or are enriched in that isomer.

Similarly, when $R^2$ is a group of formula (f), the group $A_4$ is preferably cis to the amide linkage, i.e. when group (f) is 2-amino-thiazol-4-yl, the Z-configuration is preferred.

Examples of $R^4$ groups include phthalidyl; and 2,5-dihydro-2-oxofuran-5-yl, 2-oxotetrahydrofuran-5-yl and 2-oxo-tetrahydrofuran-3-yl derivatives, each of which is optionally mono- or di-substituted by one or two groups selected from $C_{1-6}$ alkyl, for example methyl; $C_{1-6}$ alkoxy, for example methoxy, and aryl, for example phenyl.

Certain compounds of the invention include an amino group which may be protected. Suitable amino protecting groups are those well known in the art which may be removed under conventional conditions without disruption of the remainder of the molecule.

Examples of amino protecting groups include $C_{1-6}$ alkanoyl; benzoyl; benzyl optionally substituted in the phenyl ring by one or two substituents selected from $C_{1-4}$ alkyl, $C_{1-4}$ alkoxy, trifluoromethyl, halogen, or nitro; $C_{1-4}$ alkoxycarbonyl; benzyloxycarbonyl or trityl substituted as for benzyl above; allyloxycarbonyl, trichloroethoxycarbonyl or chloroacetyl.

Some of the compounds of this invention may be crystallised or recrystallised from solvents such as organic solvents. In such cases solvates may be formed. This invention includes within its scope stoichiometric solvates including hydrates as well as compounds containing variable amounts of water that may be produced by processes such as lyophilisation.

Since the antibiotic compounds of the invention are intended for use in pharmaceutical compositions it will readily be understood that they are each provided in substantially pure form, for example at least 60% pure, more suitably at least 75% pure and preferably at least 85%, especially at least 95% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 49% of a compound of the formula (I) or salt thereof.

Specific compounds within this invention of formula (Ia) include the following and pharmaceutically acceptable salts and in-vivo hydrolysable esters thereof:

7η-[2-(2-aminothiazol-4-yl)-2-Z-methoxyiminoacetamido]-3-(E-2,5-dihydro-3-methyl-2-oxofuran-5-ylidenemethyl)ceph-3-em-4-carboxylic acid, 7β-[2-(2-aminothiazol-4-yl)-2-Z-methoxyiminoacetamido]-3-[(5RS)-2,5-dihydro-2-oxofuran-5-ylmethyl]ceph-3-em-4-carboxylic acid, 7β-[2-(2-aminothiazol-4-yl)-2-Z-methoxyiminoacetamido]-3-(E-phthalidylidenemethyl)-ceph-3-em-4-carboxylic acid, 7β-[2-(2-aminothiazol-4-yl)-2-Z-methoxyiminoacetamido]-3-(E-2,5-dihydro-4-methyl-2-oxo-3-phenylfuran-5-ylidenemethyl)ceph-3-em-4-carboxylic acid, 7β-[2-(2-aminothiazol-4-yl)-2-Z-hydroxyiminoacetamido]-3-(E-2,5-dihydro-3-methyl-2-oxofuran-5-ylidenemethyl)-ceph-3-em-4-carboxylic acid, 7β-[2-(2-aminothiazol-4-yl)-2-Z-methoxyiminoacetamido]-3-(E-2,5-dihydro-4-methoxy-3-methyl-2-oxofuran-5-ylidenemethyl)ceph-3-em-4-carboxylic acid, 7β-[2-(2-aminothiazol-4-yl)-2-Z-methoxyiminoacetamido]-3-(Z-2,5-dihydro-4-methoxy-3-methyl-2-oxofuran-5-ylidenemethyl)ceph-3-em-4-carboxylic acid, 7β-[2-(2-aminothiazol-4-yl)-2-Z-methoxyiminoacetamido]-3-[(5RS)-2-oxotetrahydrofuran-5-ylmethyl]ceph-3-em-4-carboxylic acid, 7β-[2-(2-aminothiazol-4-yl)-2-Z-hydroxyiminoacetamido]-3-(Z-2,5-dihydro-4-methoxy-3-methyl-2-oxofuran-5-ylidenemethyl)ceph-3-em-4-carboxylic acid, 7β-[2-(2-aminothiazol-4-yl)-2-Z-hydroxyiminoacetamido]-3-(2,5-dihydro-2-oxofuran-5-ylmethyl)ceph-3-em-4carboxylic acid, and 7β-[2-(2-aminothiazol-4-yl)-2-Z-methoxyiminoacetamido]-3-(E-2-oxotetrahydrofuran-3-ylidenemethyl)ceph-3-em-4-carboxylic acid.

The present invention further provides a process for the preparation of a compound of formula (I), which process comprises treating a compound of formula (II) or a salt thereof:

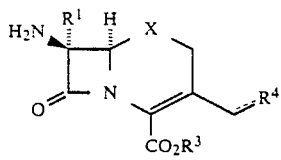  (II)

wherein $R^1$, $CO_2R^3$, $R^4$, X and the dashed line adjacent to $R^4$ are as hereinbefore defined, wherein any reactive groups may be protected, and wherein the amino group is optionally substituted with a group which permits acylation to take place; with an N-acylating derivative of an acid of formula (III):

$$R^2OH \quad \text{(III)}$$

wherein $R^2$ is as defined with respect to formula (I) and wherein any reactive groups may be protected; and thereafter, if necessary or desired, carrying out one or more of the following steps:

i) removing any protecting groups;
ii) converting the group $CO_2R^3$ into a different group $CO_2R^3$;
iii) converting the group $R^2$ into a different group $R^2$;
iv) converting the group X into a different group X;
v) reducing an $R^4$ butenolide to an $R^4$ butanolide;
vi) reducing an optional double bond adjacent to $R^4$;
vii) converting the product into a salt.

Acids of formula (III) may be prepared by methods known in the art, or methods analogous to such processes. Suitable processes include those described, for example, in UK Patent 2 107 307 B, UK Patent Specification No. 1,536,281, and U.K. Patent Specification No. 1,508,064.

Suitable groups which permit acylation to take place and which are optionally present on the amino group of the starting material of the formula (II) include N-silyl, N-stannyl and N-phosphorus groups, for example trialkylsilyl groups such as trimethylsilyl, trialkyltin groups such as tri-n-butyltin, groups of formula —P.$R^8R^9$ wherein $R^8$ is an alkyl, haloalkyl, aryl, aralkyl, alkoxy, haloalkyl, aryl, aralkyl, alkoxy, haloalkoxy, aryloxy, aralkyloxy or dialkylamino group, $R^9$ is the same as $R^8$ or is halogen or $R^8$ and $R^9$ together form a ring; suitable such phosphorus groups being —P(OC$_2$H$_5$)$_2$, —P(C$_2$H$_5$)$_2$,

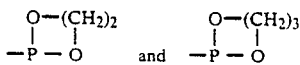

A group which may optionally be introduced onto the amino group in the compound of formula (II) is trimethylsilyl.

Advantageously the silylation reaction may be carried out in situ, prior to the acylation reaction, with a silylating agent that does not require concomitant addition of base. Suitable silylating agents include, for example, N-(trimethylsilyl)-acetamide, N,O-bis(trimethylsilyl)acetamide, N,O-bis(trimethylsilyl)trifluoroacetamide, N-methyl-N-trimethylsilylacetamide, N-methyl-N-trimethylsilyl-trifluoroacetamide, N,N'-bis(trimethylsilyl)urea, and N,O-bis(trimethylsilyl)carbamate. A preferred silylating agent is N,O-bis(trimethylsilyl)acetamide. The silylation reaction may suitably be carried out in an inert, anhydrous organic solvent such as dichloromethane at room temperature or at an elevated temperature, for example 30°-60° C., preferably 40°-50° C.

The above process may optionally be carried out in the presence of a small quantity, for example 0.1 equivalents, of a silyl halide, for example a tri(C$_{1-6}$)alkylsilyl halide, especially trimethylsilyl chloride.

A reactive N-acylating derivative of the acid (III) is employed in the above process. The choice of reactive derivative will of course be influenced by the chemical nature of the substituents of the acid.

Suitable N-acylating derivatives include an acid halide, preferably the acid chloride or bromide. Acylation with an acid halide may be effected in the presence of an acid binding agent for example, tertiary amine (such as pyridine or dimethylaniline), molecular sieves, an inorganic base (such as calcium carbonate or sodium bicarbonate) or an oxirane, which binds hydrogen halide liberated in the acylation reaction. The oxirane is preferably a (C$_{1-6}$)- 1,2-alkylene oxide—such as ethylene oxide or propylene oxide. The acylation reaction using an acid halide may be carried out at a temperature in the range −50° C. to +50° C., preferably −20° C. to +20° C., in aqueous or non-aqueous media such as water, acetone, tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (III) or a salt or a reactive derivative thereof with a halogenating (eg chlorinating or brominating) agent such as phosphorus pentachloride, thionyl chloride, oxalyl chloride or phosgene.

Alternatively, the N-acylating derivative of the acid (III) may be a symmetrical or mixed anhydride. Suitable mixed anhydrides are anhydrides with, for example, carbonic acid monoesters, trimethyl acetic acid, thioacetic acid, diphenylacetic acid, benzoic acid, phosphorus acids (such as phosphoric, phosphorous, and phosphinic acids) or aromatic or aliphatic sulphonic acids (such as p-toluenesulphonic acid or methanesulphonic acid). When a symmetrical anhydride is employed, the reaction may be carried out in the presence of 2,6-lutidine as catalyst.

Alternative N-acylating derivatives of acid (III) are the acid azide, or activated esters such as esters with 2-mercaptopyridine, cyanomethanol, p-nitrophenol, 2,4-dinitrophenol, thiophenol, halophenols, including pentachlorophenol, monomethoxyphenol, N-hydroxy succinimide, N-hydroxybenzotriazole, or 8-hydroxyquinoline; or amides such as N-acylsaccharins, N-acylthiazolidin-2-thione or N-acylphthalimides; or an alkylidene iminoester prepared by reaction of the acid (III) with an oxime.

Other reactive N-acylating derivatives of the acid (III) include the reactive intermediates formed by reaction in situ with a condensing agent such as a carbodiimide, for example, N,N'-diethyl-, dipropyl- or diisopropylcarbodiimide, N,N'-di-cyclohexylcarbodiimide, or N-ethyl-N'-[3-(dimethylamino)propyl]-carbodiimide; a suitable carbonyl compound, for example, N,N'-carbonyldiimidazole or N,N'-carbonylditriazole; an isoxazolinium salt, for example, N-ethyl-5-phenylisoxazolinium-3-sulphonate or N-t-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3$—$C_6H_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

A further method of forming the N-acylating derivative of the acid of formula (III) is to treat the acid of formula (III) with a solution or suspension preformed by addition of a carbonyl halide, preferably oxalyl chloride, or a phosphoryl halide such as phosphorus oxychloride, to a halogenated hydrocarbon solvent, preferably dichloromethane, containing a lower acyl tertiary amide, preferably N,N-dimethylformamide. The N-acylating derivative of the acid of formula (III) so derived may then be caused to react with a compound of formula (II). The acylation reaction may conveniently be carried out at −40° to +30° C., if desired in the presence of an acid binding agent such as pyridine. A catalyst such as 4-dimethylaminopyridine may optionally also be added. A preferred solvent for the above acylation reaction is dichloromethane.

The optional reduction steps, the optional conversion of $R^2$ to a different $R^2$, $CO_2R^3$ to a different $CO_2R^3$ and X to a different X, and the optional formation of a salt, may be carried out using methods well known in the art of cephalosporin and penicillin chemistry.

For example, when the group X is S, SO, or $SO_2$, the group X may be converted into a different group X by methods of oxidation or reduction well known in the art of cephalosporin and penicillin synthesis, as described, for example, in European Patent Application Publication No. 0 114 752. For example, sulphoxides (in which X is SO) may be prepared from the corresponding sulphide (in which X is S) by oxidation with a suitable oxidising agent, for example an organic peracid such as m-chloroperbenzoic acid.

Reduction steps are generally effected by process of catalytic hydrogenation in the presence of a suitable catalyst or combination thereof.

In the process described hereinabove, and in the processes described hereinbelow, it may be necessary to remove protecting groups. Deprotection may be carried out by any convenient method known in the art such that unwanted side reactions are minimised. Separation of unwanted by-products may be carried out using standard methods.

Compounds of formula (II) are novel compounds and as such form part of the invention. Compounds of formula (II) may be prepared by removal of $R^2$ from compounds of formula (I) prepared by the processes described hereinbelow.

In a further process of the invention, compounds of formula (I) may be prepared by treating a compound of formula (IV):

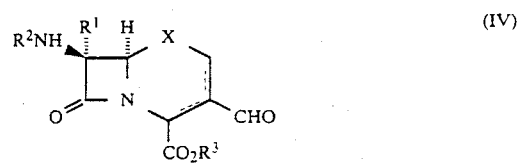

(IV)

wherein X, $R^1$, $R^2$ and $CO_2R^3$ are as hereinbefore defined and the dashed line represents a double bond in the 2- or 3-position of the cephalosporin nucleus, with a phosphorus ylid compound of formula (V):

$$P'=R^4 \quad (V)$$

wherein P' is the phosphorus residue and $R^4$ is as hereinbefore defined; and thereafter if necessary or desired, carrying out one or more of the following steps:

i) removing any protecting groups;
ii) converting the group $CO_2R^3$ into a different group $CO_2R^3$;
iii) converting the group $R^2$ into a different group $R^2$;
iv) converting the group X into a different group X;
v) reducing an $R^4$ butenolide to an $R^4$ butanolide;
vi) reducing an optional double bond adjacent to $R^4$;
vii) converting the product into a salt.

The reaction between a compound of formula (Iv) and a phosphorus ylid of formula (V) is a Wittig-type reaction and is typically carried out at ambient temperature in an inert solvent such as dichloromethane.

The phosphorus ylid of formula (V) is typically a phosphonium ylid (or phosphorane). Suitable phosphonium ylids include compounds of formula (V) in which P' is a trialkylphosphoranylidene residue, for example a $C_{1-6}$ trialkylphosphoranylidene residue such as tri-n-butylphosphoranylidene, or a triarylphosphoranylidene residue such as triphenylphosphoranylidene.

Phosphonate reagents may also be used. These include compounds containing a dialkylphosphonate residue, for example a di-$C_{1-6}$ alkylphosphonate residue such as diethylphosphonate.

A phosphonium ylid may be prepared in situ by the action of base, for example sodium hydride, on the corresponding phosphonium halide, for example the corresponding phosphonium bromide, in dimethylsulphoxide.

Compounds of formula (V) may be prepared by methods well known in the art of phosphorus chemistry.

The preparation of a phosphonium ylid compound of formula (V) in which $R^4$ is mono- or di-substituted 2,5-dihydro-2-oxofuran-5-yl is illustrated in Scheme I below for the compound of formula (V) in which P' is triphenylphosphoranylidene and $R^4$ is 2,5-dihydro-3-methyl-2-oxofuran-5-yl.

Scheme I

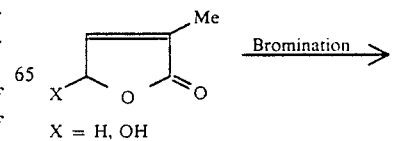

X = H, OH

-continued
Scheme I

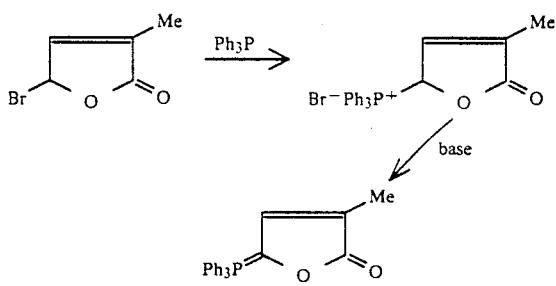

In yet a further process of the invention, compounds of formula (I) wherein the optional double bond adjacent to $R^4$ is absent may be prepared by treating a compound of formula (VI):

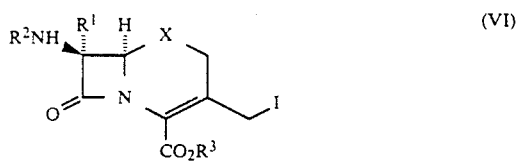

(VI)

wherein $R^1$ $R^2$, $CO_2R^3$ and X are as hereinbefore defined, with a compound of formula (VII):

(VII)

wherein the furan ring is optionally substituted as hereinbefore defined for $R^4$ in formula (I); and thereafter, if necessary or desired carrying out one or more of the following steps:
  i) removing any protecting groups;
  ii) converting the group $CO_2R^3$ into a different group $CO_2R^3$;
  iii) converting the group $R^2$ into a different group $R^2$;
  iv) converting the group X into a different group X;
  v) reducing the $R^4$ butenolide to an $R^4$ butanolide;
  vi) converting the product into a salt.

The reaction is typically carried out at a depressed temperature e.g. $-78°$ C. in the presence of silver trifluoroacetate suspended in an inert solvent such as dichloromethane, and in an inert atmosphere e.g. under argon. See C. W. Jefford, A. W. Sledeski and J. Boukouvalas, *J. Chem. Soc., Chem. Commun.*, 1988, 364.

Compounds of formula (VI) may be prepared from the corresponding 3-chloromethyl derivative by treatment with sodium iodide in acetone. Trimethylsilyloxyfuran compounds of formula (VII) are commercially available or may be prepared by treatment of the corresponding butenolide derivative with trimethylchlorosilane in the presence of an appropriate base.

It should be noted that in processes of this invention $\Delta^2$-cephems, for example compounds of formula (IV), may function as intermediates, in the synthetic sequences. Subsequent isomerisation steps by methods well known in cephalosporin chemistry will provide the $\Delta^3$-cephems of the invention.

The present invention also provides a pharmaceutical composition which comprises a compound of formula (Ia) or a pharmaceutically acceptable salt or in vivo hydrolysable ester thereof and a pharmaceutically acceptable carrier. The compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing. Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (Ia) or a pharmaceutically acceptable salt or in vivo hydrolysable ester thereof is administered in the above-mentioned dosage range.

The compound of formula (Ia) may be the sole therapeutic agent in the compositions of the invention or a combination with other antibiotics or with a β-lactamase inhibitor may be employed.

Advantageously, the compositions also comprise a compound of formula (VIII) or a pharmaceutically acceptable salt or ester thereof:

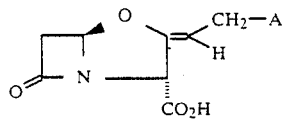

(VIII)

wherein

A is hydroxyl, substituted hydroxyl, thiol, substituted thiol, amino, mono- r dihydrocarbylsubstituted amino, or mono- or di-acylamino.

A further advantageous composition comprises a compound of formula (Ia) or a pharmaceutically acceptable salt or in vivo hydrolysable ester thereof together with a compound of formula (IX) or a pharmaceutically acceptable salt or in vivo hydrolysable ester thereof:

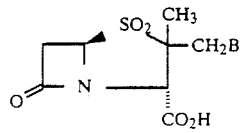

(IX)

wherein

B represents hydrogen or chloro.

Further suitable β-lactamase inhibitors include 6β-bromopenicillanic acid and pharmaceutically acceptable salts and in vivo hydrolysable esters thereof and 6β-iodopenicillanic acid and pharmaceutically acceptable salts and in vivo hydrolysable esters thereof described in, for example, EP-A-0 410 768 and EP-A-0 154 132 (both Beecham Group).

Such compositions of this invention which include a β-lactamase inhibitory amount of a β-lactamase inhibitor are formulated in a conventional manner using techniques and procedures per se known in the art.

The present invention provides a compound of formula (Ia) or a pharmaceutically acceptable salt or in vivo hydrolysable ester thereof, for use as a therapeutic agent.

The present invention further provides a compound of formula (Ia) or a pharmaceutically acceptable salt or in vivo hydrolysable ester thereof, for use in the treatment of bacterial infections.

The present invention also includes a method of treating bacterial infections in humans and animals which comprises the administration of a therapeutically effective amount of an antibiotic compound of this invention of the formula (Ia) or a pharmaceutically acceptable in vivo hydrolysable ester thereof.

In addition, the present invention includes the use of a compound of formula (Ia) or a pharmaceutically acceptable salt or in vivo hydrolysable ester thereof, in the manufacture of a medicament for the treatment of bacterial infections.

The antibiotic compounds of the present invention are active against a wide range of organisms including both Gram-negative organisms such as *E. coli* and Gram-positive organisms such as *S.aureus*.

The following Examples illustrate the preparation of the compounds of the present invention and the following biological data illustrate the activity of compounds of the invention in the form of M.I.C. results against a sample *E. coli* organism (NCTC 10418) and a sample *S.aureus* organism (*S.aureus* Oxford).

EXAMPLE 1

Sodium 7β-2-(2-Aminothiazol-4-yl)-2-Z-methoxyiminoacetamido]-3-(E-2,5-dihydro-3-methyl-2-oxofuran-5-ylidenemethyl)ceph-3-em-4-carboxylate.

(a) Diphenylmethyl 3-(E-2,5-dihydro-3-methyl-2-oxofuran-5-ylidenemethyl)-7β-phenylacetamidoceph-3-em-4-carboxylate.

Method 1

2,5-Dihydro-5-hydroxy-3-methyl-2-oxofuran (G. Pattenden and B. C. L. Weedon, *J.Chem.Soc.(C)*, 1968,1984) was readily converted to 2,5-dihydro-4-methyl-5-oxofuran-2-yl(triphenyl)phosphonium bromide, by successive treatment with phosphorus tribromide and triphenylphosphine (D. W. Knight and G. Pattenden, *J.Chem.Soc., Perkin Trans.I.* 1975,635). The corresponding phosphorane was obtained immediately prior to use by dissolving the phosphonium salt in water and adjusting the pH to ca 7, with aqueous sodium hydroxide. The yellow, precipitated phosphorane was filtered, washed and dried. Diphenylmethyl 3-formyl-7β-phenylacetamidoceph-3-em-4-carboxylate (0.629g), (British patent no. 1,342, 241, 1974) in dry dichloromethane (10 mls) was treated with the phosphorane (0.44 g) at room temperature for ca 30 mins. T.l.c. analysis showed conversion to a more polar product. The reaction mixture was concentrated and purified by flash chromatography on silica gel, eluting with 40,50 and 60% ethyl acetate/hexane. The title compound was crystallized by trituration with methanol, (0.138g 19%), m.p. 193°–197° C.(decomp.), ethyl acetate/hexane). (Found: C,68.97; H, 4.95; N, 4.85%. $C_{34}H_{28}N_2O_6S$ requires C, 68.90; H, 4.76; N, 4.73%); $\mu_{max}(CH_2Cl_2)$ 3400 (w), 1785 (shoulder), 1765, 1720, 1680, 1490 and 1365cm$^{-1}$; $\delta_H$ (CDCl$_3$) 1.90 (3H, d, J0.7Hz), 3.48 (2H, ABq, J17.7Hz), 3.62 (2H, ABq, J16.0Hz), 5.01 (1H, d, J4.9Hz), 5.89 (1H, dd, J4.9, 9.0Hz), 6.31 (1H, d, J9.0Hz), 6.52 (1H, br.s,), 6.94 (1H, s), 7.08 (1H, br.s) and 7.35 (15H, m); [mass spectrum: +ve ion (3NOBA, Na$^+$) MNa$^+$, 615].

Method 2

Sodium hydride (0.094g) was dissolved in warm dry dimethyl sulphoxide (10mls), under argon, to give a clear grey/green solution. At room temperature this was treated with a solution of 2,5-dihydro-4-methyl-5-oxofuran-2-yl(triphenyl)phosphonium bromide (1.72g) in dimethyl sulphoxide (5mls) to give a yellow suspension of the phosphorane generated in situ. After 30 mins, a solution of diphenylmethyl 3-formyl-7η-phenylacetamidoceph-3-em-4-carboxylate (2 g) in dimethyl sulphoxide (5 mls) was added. The reaction was monitored by t.l.c. analysis until all the aldehyde had been consumed, ca 75 mins. The reaction mixture was poured into a mixture of 5M hydrochloric acid (100 mls) and ethyl acetate (100 mls). The organic phase was separated and washed with dil. hydrochloric acid, water and brine. After drying and removal of solvent the brown gum was dissolved in methanol (5 mls) and left overnight refrigerated. The title compound was removed by filtration, washed with a little methanol, ether and then dried, (0.605g, 26%).

(b) Diphenylmethyl 7β-Amino-3-(E-2,5-dihydro-3-methyl-2-oxofuran-5-ylidenemethyl)ceph-3-em-4-carboxylate.

Diphenylmethyl 3-(E-2,5-dihydro-3-methyl-2-oxo-5-ylidene methyl-7β-phenylacetamidoceph-3-em-4-carboxylate (0.49 g) in dichloromethane (10mls), cooled to −20° C. under argon was treated with N-methylmorpholine (0.184 g, 0.2 mls) and finely ground phosphorous pentachloride (0.224 g, resublimed 100° C. at 0.1 mm Hg), for 30 mins. I.r. analysis showed very little starting material. Methanol (dry, 5 mls) was added rapidly in one portion and the reaction allowed to warm from −20° C. to room temperature over 30 mins. Water (10 mls) was then added. The dichloromethane was removed in vacuo and replaced with ethyl acetate. The pH was adjusted to 8 with saturated aqueous sodium hydrogencarbonate. The aqueous phase was further extracted with ethyl acetate. The combined organic phases were then washed with water and brine, dried and concentrated. The product was obtained by flash chromatography eluting with ethyl acetate, as a pale yellow solid, (0.127 g, 32%), $v_{max}$(CH$_2$Cl$_2$) 3400 (v.w), 1780 (shoulder), 1760, 1720, 1610, 1560 (w), 1490 (w), 1380 and 1360cm$^{-1}$; $\delta_H$(CDCl$_3$) 1.88 (3H, d, J0.4Hz), 3.54 (2H, ABq, J17.6Hz), 4.84 (1H, d, J5.1Hz), 5.03 (1H, d, J5.1Hz), 6.43 (1H, s), 7.00 (1H, s), 7.04 (1H, d, J0.8Hz), 7.32 (10H, m); [mass spectrum: +ve ion (3NOBA, Na$^+$) MNa$^+$, 497].

(c) Diphenylmethyl 7β-[2-(2-Aminothiazol-4-yl)-2-Z-methoxyiminoacetamido]-3-(E-2,5-dihydro-3-methyl-2-oxofuran-5-ylidenemethyl)ceph-3-em-4-carboxylate 2-(2-Aminothiazol-4-yl)-2-Z-methoxyiminoacetic acid (0.042 g) in dry DMF (1-2 mls) under argon, was cooled to −50° C. and treated in turn with diisopropylethylamine (0.035 g; 0.047 mls) and methanesulphonyl chloride methyl 7β-amino-3-(E-2,5-dihydro-3-methyl-2-oxofuran-5-ylidenemethyl)ceph-3-em-4-carboxylate (0.108 g) in dry dichloromethane (2mls), with triethylamine (0.023 g; 0.032 mls) was added to the activated intermediate at −50° C. and then allowed to warm to room temperature. The solution monitored by t.l.c. analysis showed only one product. The reaction mixture was diluted with dichloromethane and washed with water and brine. After drying and removal of solvent, the residue was purified by flash chromatography on silica gel to give the title compound as a yellow solid, (0.093 g, 65%); $v_{max}$(CH$_2$Cl$_2$) 3650 (vw), 3470 (vw), 3400 (w) 1780 (Shoulder), 1760, 1720, 1680 (shoulder), 1675, 1600, 1520 (br) and 1365cm$^{-1}$; $\delta_H$ (CDCl$_3$) 1.88 (3H, s), 3.56 (2H, ABq, J17.8Hz), 4.07 (3H, S), 5.18 (1H, d, J4.9Hz), 5.46 (2H, br.s), 6.10 (1H, dd, J4.9, 8.9Hz), 6.50 (1H,s), 6.82 (1H.s), 6.98 (1H, s), 7.03 (1H, br,s), 7.33 (10H, m) and 7.86 (1H, d, J8.9Hz); [mass spectrum: +ve ion (3NOBA) MH$^+$, 658].

(d) Sodium 7β-[2-(2-Aminothiazol-4-yl)-2-Z-methoxyiminoacetamido[-3-(E-2,5-dihydro-3-methyl-2-oxofuran-5-ylidenemethyl)ceph-3-em-4-carboxylate.

Diphenylmethyl 7β-[2-(2-aminothiazol-4-yl)-2-Z-methoxyiminoacetamido]-3-(E-2,5-dihydro-3-methyl-2-oxofuran-5-ylidenemethyl)ceph-3-em-4-carboxylate (0.09 g) in trifluoroacetic acid (2 mls) was stirred at room temperature for 15 mins. The solvent was removed in vacuo and the residual gum triturated with ether. The solid was dissolved in saturated aqueous sodium hydrogen carbonate and chromatographed on HP20SS eluting with 200mls portions of 0,2 and 4% THF/water. The fractions containing the product as monitored by h.p.l.c. were combined, concentrated and freeze-dried. The title compound was obtained as a yellow foam, (0,035g; 48%); $\lambda_{max}$ (H20) 362 ($\epsilon$21740), and 230nm ($\epsilon$15110); $v_{max}$ (KBr) 1741 (br), 1679, 1610, 1528 and 1387cm$^{-1}$; $\delta_H$ (D$_2$O) 1.95 (3H,s), 3.72 (2H, ABq, J17.1Hz), 3.97 (3H,s), 5.29 (1H, d, J4.8Hz), 5.82(1H, d, J4.8Hz), 6.56 (1H, br,s), 6.97 (1H.s) and 7.56 (1H, br,s); [mass spectrum: +ve ion (thioglycerol) MH$^+$(514), MNa$^+$, 536].

EXAMPLE 2

Sodium 7β-2-(2-Aminothiazol-4-yl)-2-Z-methoxyiminoacetamidol-3-[(5RS)-2,5-dihydro-2-oxofuran-5ylmethyl-[ceph-3-em-4-carboxylate.

(a) Diphenylmethyl 3-(5RS)-2,5-dihydro-2-oxofuran-5-ylmethyl]-7β-phenylacetamidoceph-3-em-4-carboxylate.

Diphenylmethyl 3-chloromethyl-7β-phenylacetamidoceph-3-em-4-carboxylate (1 g) in pure acetone (20 mls) and sodium iodide (0.31 g) were stirred at room temperature for 2 h. The solution was filtered through 'celite' and the acetone evaporated in vacuo. The residue was dissolved in ethyl acetate and washed successively with water, aq. sodium thiosulphate and brine. After drying and removal of solvent the iodo compound was obtained, sufficiently pure, as a pale yellow foam. A solution of diphenylmethyl 3-iodomethyl-7β-phenyl-acetamidoceph-3-em-4-carboxylate (1 g) and 2-trimethylsiloxyfuran (0.25 g; 0.264 mls) in dichloromethane (5 mls), was added to a suspension of silver trifluoroacetate (0.354 g) in dichloromethane (5 mls) at −78° C., under argon. The reaction mixture was allowed to warm, slowly, to room temperature and then washed with dilute hydrochloric acid, water and brine. The solution was dried and concentrated to a small volume. Flash chromatography on silica gel with 50,60% ethyl acetate/hexane afforded the title compound as a pale yellow gum which solidified on trituration with ether, (0.247 g,27%); $\nu_{max}$(KBr) 3307 (br), 1774, 1760 (shoulder), 1719, 1662, 1601, 1523, 1493, 1452, and 1374cm$^{-1}$; $\delta_H$ (CDCl$_3$) major isomer 2.09 (1H, dd, J9.3, 13.7Hz), 3.16 (1H, dd, J2.6, 13.7Hz), 3.52 (2H, ABq, J9.7Hz), 3.65 (2H, s), 4.94 (1H, d, J4.9Hz), 5.21 (1H, m), 5.89 (1H, dd, J4.9, 9.0Hz), 6.05 (1H, dd, J1.8, 5.7Hz), 6.15 (1H, d, J9.0Hz), 6.86 (1H,s), 7.21 (1H, dd, J1.3, 5.7Hz), and 7.32 (15H, m); minor isomer inter alia 2.70 (1H, dd, J7.3H, 13.9Hz), 3.67 (2H, s), 4.96 (1H, d, J4.8Hz), 5.04 (1H, m), 6.14 (1H, d, J9.0Hz), and 6.87 (1H, s); [mass spectrum: +ve ion (3NOBA, Na$^+$)MNa$^+$, 603].

(b) Diphenylmethyl 7β-Amino-3-[(5RS)-2,5-dihydro-2-oxofuran-5-ylmethyl[ceph-3-em-4-carboxylate.

Diphenylmethyl 3-[(5RS)-2,5-dihydro-2-oxofuran-5ylmethyl]-7β-phenylacetamidoceph-3-em-4-carboxylate (0.23 g) in dry dichloromethane (5 mls) under argon, was cooled to −20° C. and treated with N-methylmorpholine (0.088 g; 0.096 mls) followed by finely powdered phosphorous pentachloride. After ca 45 mins i.r. analysis showed no starting material. Dry methanol (5 mls) was added rapidly and the reaction mixture allowed to warm to room temperature over 30 mins. Water (5 mls) was then added, left at room temperature for a further 30 mins. The dichloromethane was removed in vacuo, the pH adjusted to 8 and extracted with portions of ethyl acetate. The combined ethyl acetate extracts were washed with water, brine and then dried. Removal of solvent gave a brown gum, t.l.c. analysis showing one major product. Purification by silica gel flash chromatography afforded the title compound as a pale yellow foam, (0.096 g, 52%); $\nu_{max}$(CH$_2$Cl$_2$) 3400 (v.w), 1770 (br), 1720 and 1610cm$^{-1}$; $\delta_H$(CDCl$_3$) major isomer 2.26 (1H, dd, J9.8, 13.8Hz), 3.09 (1H, dd, J3.0, 13.8Hz), 3.57 (2H, ABq, J18.5Hz), 4.79 (1H, d, J4.7Hz), 4.93 (1H, d, J4 7Hz), 5.22 (1H, m), 6.03 (1H, dd, J1.8, 5.6Hz), 6.91 (1H, s), 7.12 (1H, br.d, J5.6Hz) and 7.35 (15H, m); minor isomer inter alia 2.67 (1H, dd, J7.5, 13.9Hz), 4.65 (1H, m), 4.97 (1H, d, J4.8Hz) and 6.93 (1H, s); [mass spectrum: +ve ion (3NOBA, Na$^+$) MNa$^+$, 485].

(c) Diphenylmethyl 7β-[2-(2-Aminothiazol-4-yl)-2-Z-methoxyiminoacetamido]-3-[(5RS)-2,5-dihydro-2-oxofuran-5 -ylmethyl]ceph-3-em-4-carboxylate.

2-(2-Aminothiazol-4-yl)-2-Z-methoxyiminoacetic acid (0.035 g) was reacted with methanesulphonyl chloride (0.025 g, 0.017 mls) and diisopropylethylamine (0.029 g, 0.038 mls), in DMF (0.5 mls) as described in Example 1(c). This was coupled with diphenylmethyl 7⊕-amino-3-[(5RS)-2,5-dihydro-2-oxofuran-5-ylmethyl]ceph-3-em-4-carboxylate (0.085 g) in dichloromethane (1.5 mls). After the same work up procedure the crude product was purified by silica gel flash chromatography to give the title compound as a pale yellow solid, (0.096 g, 82%); $\nu_{max}$ 3460 (w), 3370 (w), 1760 (v.br), 1720, 1680, 1610 (shoulder), 1600, 1520 and 1370cm$^{-1}$; $\delta_H$(CDCl$_3$) 2.22 (1H, dd, J9.0, 13.7Hz), 3.18 (1H, dd, J1.9, 13.7Hz), 3.61 (2H, ABq, J20.6Hz), 4.09 (3H, s), 5.07 (1H, d, J4.9Hz) 5.24 (1H, m), 5.37 (3H, br.s, exch.), 6.04 (2H, m), 6.90 (1H, s), 6.94 (1H, s), 7.19 (1H, dd, J1.3, 5.8Hz), 7.48 (10H, m), minor isomer inter alia 2.73 (1H, dd, J7.4, 14.0Hz), 4.10 (3H, s), 4.66 (1H, m), 6.86 (1H, s) and 6.91 (1H, s); [mass spectrum: +ve ion (3NOBA, Na$^+$) MNa$^+$, 668].

(d) Sodium 7β-[2-(2-Aminothiazol-4-yl)-2-Z-methoxyiminoacetamido]-3-[(5RS)-2,5-dihydro-2-oxofuran-5ylmethyl]ceph-3-em-4-carboxylate.

Diphenylmethyl 7β-[2-(2-aminothiazol-4-yl)-2-Z-methoxyiminoacetamido]-3-[(5RS)-2,5-dihydro-2-oxofuran-5ylmethyl]ceph-3-em-4-carboxylate (0.086 g) was deprotected and purified as described in Example 1(d). The title compound was obtained as a white foam. (0.02 g, 30%); $\nu_{max}$ (KBr) 1750 (br), 1663, 1601 (v,br), 1532, 1458 and 1365cm$^{-1}$; $\delta_H$(D$_2$O) 2.78 (1H, dd, J4.3, 14.5Hz), 2.95 (1H, dd, J7.6, 14.5Hz), 3.48 (2H, ABq, J17.6Hz), 3.95 (3H, s), 5.16 (1H, dd, J4.8Hz), 5.45 (1H, m), 5.73 (1H, d, J4.8Hz), 6.17 (1H, d, J1.8, 5.8Hz), 7.00 (1H, s) and 7.70 (1H, dd, J1.3, 5.8Hz); minor isomer inter alia 2.58 (1H, dd, J7.0, 14.4Hz), 5.36 (1H, m), 6.99 (1H, s) and 7.74 (1H, d, J5.8Hz);
[mass spectrum: +ve ion (thioglycerol) MH$^+$, 502, MNa$^+$, 524].

EXAMPLE 3

Pivaloyloxymethyl 7β-[2-(2-Aminothiazol-4-yl)-2-Z-methoxyiminoacetamido[-3-(E-2,5-dihydro-3-methyl-2-oxofuran-5-ylidenemethyl)ceph-3-em-4-carboxylate Pivaloyloxymethyl bromide (0.055 g) in acetone (1 ml) was treated with dry sodium iodide at room temperature for 30 mins. The solvent was then removed in vacuo. To the residue was added a solution of sodium 7β-[2-(2-aminothiazol-4-yl)-2-Z-methoxyiminoacetamido]-3-(E-2,5-dihydro-3-methyl-2-oxofuran-5-ylidenemethyl)-ceph-3-em-4-carboxylate (0.145 g) in dry DMF (3 mls). The reaction was stirred at room temperature for 30 mins, and then diluted with ethyl acetate, washed with water and brine, dried and evaporated. The crude residue was flash chromatographed on silica gel eluting with 80% ethyl acetate/hexane to afford the title compound as a yellow amorphous solid; (0.096 g, 56%); $\lambda_{max}$ (EtOH) 360($\epsilon$25254), and 234 nm (18100); $\nu_{max}$(CH$_2$Cl$_2$) 3450 (w), 3300 (w,br), 1760 (br), 1680, 1600, 1520 and 1365cm$^{-1}$; $\delta_H$ (CDCl$_3$) 1.24 (9H, s), 2.08 (3H, s), 3.68 (2H, ABq, J17.5Hz), 4.08 (3H, s), 5.19 (1H, d, J5.0Hz), 5.44 (1H, br.s, exch), 5.87 (2H, ABq, J5.5Hz), 6.06 (1H, dd, J4.9, 8.9Hz; with D$_2$O collapses to d, J4.9Hz), 6.81 (1H, s), 6.85 (1H, s), 7.28 (1H, s), and 7.72 (1H, d, J8.9Hz, exch); [mass spectrum: +ve ion (thioglycerol) MH$^+$606].

EXAMPLE 4

Pivaloyloxymethyl 7β-[2-(2-Aminothiazol-4-yl)-2-Z methoxyiminoacetamido]-3-[(5RS)-2,5-dihydro-2-oxofuran-5-ylmethyl]ceph-3-em-4-carboxylate The title compound was prepared as described in Example 3, using pivaloyloxymethyl bromide (0.051 g) in acetone (1ml), sodium iodide (0.039 g) and sodium 7β-[2-(2-aminothiazol-4-yl)-2-Z-methoxyiminoacetamido]-3-[(5RS)-2,5-dihydro-2-oxofuran-5-ylmethyl]ceph-3-em-4-carboxylate (0.13 g) in DMF (2 mls).

After purification by 'flash' silica gel chromatography, the product was obtained as a colourless amorphous solid, (0.055 g, 36%); $\nu_{max}$ (CH$_2$Cl$_2$) 3450 (w), 3400 (w,br), 1750 (v.br), 1680, 1600, 1520 and 1365cm$^{-1}$; $\delta_H$ (CDCl$_3$) major isomer 1.24 (9H, s), 2.18 (1H, dd, J9.5, 13.6Hz), 3.23 (1H, dd, J2.4, 13.7Hz), 3.66 (2H, ABq, J18.9Hz), 4.07 (3H, s), 5.08 (1H, d, J4.7Hz), 5.34 (1H, m), 5.43 (2H, br.s), 5.91 (2H, ABq, J5.8Hz), 6.03 (1H, dd, J4.7, 8.8Hz), 6.19 (1H, dd, J1.9, 5.7Hz), 6.87 (1H, s), 7.52 (1H, d, J9.0Hz), and 7.59 (1H, dd, J1.3, 5.8Hz); minor isomer inter alia 2.87 (1H, dd, J6.8, 13.9Hz), 3.52 (2H, ABq, J18.6Hz), 4 06 (3H, s), 5.61 (1H, d, J3.9Hz), 5.47 (1H, s), 5.84 (2H, s), 6.15 (1H, dd, J1.9, 5 7Hz), and 6.85 (1H, s).

EXAMPLE 5

Sodium 7β-[2-(2-Aminothiazol-4-V])-2-Z-methoxyiminoacetamido[-1-3-(E-phthalidylidenemethyl)ceph-3-em-4-carboxylate (a) Diphenylmethyl 7β-Phenylacetamido-3-(E-phthalidylidenemethyl)ceph-3-em-4-carboxylate Triphenyl(phthalidyl)phosphonium bromide (2.22 g), (D. W. Knight and G. Pattenden, *J.Chem.Soc., Perkin Trans.I.* 1975, 635) and diphenylmethyl 3-formyl-7β-phenylacetamidoceph-3-em-4-carboxylate (2 g) were dissolved in dichloromethane (60 mls). To this solution was added saturated aqueous sodium hydrogen carbonate (20 mls) and the mixture vigorously stirred at room temperature. After 5 mins, t.l.c. analysis showed all the starting material had been consumed. The organic layer was separated, washed with diluted hydrochloric acid, brine and then dried. After removal of solvent the residue was purified by flash chromatography on silica gel, eluting with 50% ethyl acetate/hexane. The pure title compound was obtained as a yellow foam, (1 g, 41%), $\nu_{max}$ (CH$_2$Cl$_2$) 3400(vw), 1780, 1720(w), 1680 (w), 1490(w) and 1365(w)cm$^{-1}$; $\delta_H$ (CDCl$_3$) 3.50 (2H,ABq;J18.5Hz), 3.69 (2H,ABq,16.2Hz), 5.32 (1H,d,J4.9Hz), 5.97 (1H,dd,J4.9,8.9Hz), 6.14 (1H,d,J8.9Hz), 6.36 (1H,s), 6.85 (1H,s), 7.1–7.5 (16H,m), 7.58 (2H,m), and 7.87 (1H,d,J6.7Hz); [mass spectrum: +ve ion (3-NOBA, Na$^+$) MNa$^+$,651].

(b) Diphenylmethyl 7β-Amino-3-(E-phthalidylidenemethyl)ceph-3-em-4-carboxylate

Diphenylmethyl 7β-phenylacetamido-3-(E-phthalidylidenemethyl)ceph-3-em-4-carboxylate (1.3 g), dissolved in dichloromethane (10 mls) was cooled to −20° C. under argon. N-methylmorpholine (0.5ml) followed by a solution of phosphorous pentachloride (0.561 g) in dichloromethane (15 mls) were then added. After ca 30 mins, i.r. analysis showed no starting material. Dry methanol (10 mls) was added in one portion very rapidly, and the solution allowed to warm to room temperature over 30 mins. Water (20 mls) was added and the mixture vigorously stirred for 20–30 mins. After washing and drying the organic phase, the crude product was purified by flash chromatography, eluting with 70 and 80% ethyl acetate/hexane. The title compound was obtained as a pale yellow solid, (0.563 g, 53%), $\nu_{max}$ (CH$_2$Cl$_2$) 1780(s), 1720, 1600(w,br), 1560 and 1210cm$^{-1}$; $\delta_H$ (CDCl$_3$) 3.56 (2H,ABq,J18.7Hz), 4.93 (1H,d,J5.1Hz), 5.10 (1H,d,J5.1Hz), 6.39(1H,s), 6.88 (1H,s), 7.21 (10H,m), 7.46–7.68 (3H,m), and 7.87 (1H,d,J7.6Hz); [mass spectrum: +ve ion (3-NOBA, Na$^+$) M Na$^+$, 532].

(c) Diphenylmethyl 7β-[2-(2-Aminothiazol-4-yl)-2-Z-methoxyiminoacetamido1-3-(E-phthalidylidenemethyl)ceph-3-em-4-carboxylate 2-(2-Aminothiazol-4-yl)-2-Z-methoxyiminoacetic acid (0.018 g) in dry DMF (2 mls) under argon was cooled to −50° C. and treated successively with diisopropylethylamine (0.091 mls) and methanesulphonyl chloride (0.04 mls) for 1 h. A solution of diphenylmethyl 7β-amino-3-(E-phthalidylidenemethyl)ceph-3-em-4-carboxylate (0.222 g) in dichloromethane (3 mls) and pyridine (0.035 mls) was added to the activated intermediate at −50° C. and the solution then allowed to warm slowly to room temperature. The solution was diluted with dichloromethane and washed with water and brine, and then dried. After removal of solvent, the crude product was purified by flash chromatography on silica gel, eluting with ethyl acetate. The title compound was obtained as a yellow amorphous solid, (0.051 g), 17%), $\nu_{max}$ (CH$_2$Cl$_2$) 1780(s), 1720(w), 1680(w), 1600(w), 1520(w br) and 1365cm$^{-1}$; $\delta_H$ (CDCl$_3$) 3.59 (2H,ABq,J18.6Hz), 4.09 (3H,s), 5.28(1H,d,J4.9Hz), 5.48 (2H,br.s, exch.), 6.20 (1H,dd,J4.9,8.9Hz; collapses to d on D$_2$O shake, J4.9Hz), 6.42 (1H,s), 6.83 (1H,s), 6.88(1H,s), 7.22 (10H,m), 7.4–7.6 (3H,m), 7.86 (1H,m) and 7.98 (1H,d,J8.9Hz, exch.); [mass spectrum: +ve ion (3-NOBA, Na$^+$) MNa$^+$, 716].

(d) Sodium 7β-2-(2-Aminothiazol-4-yl)-2-Z-methoxyiminoacetamido[-3-(E-phthalidylidenemethyl)ceph-3-em-4-carboxylate Diphenylmethyl, 7β-[2-(2-aminothiazol-4-yl)-2-Z-methoxyiminoacetamido]-3-(E-phthalidylidenemethyl)-ceph-3-em-4-carboxylate (0.286 g) was dissolved in trifluoroacetic acid (5 mls) at room temperature. After 5 mins the trifluoroacetic acid was removed in vacuo, replaced with toluene, and re-evaporated. The residue was triturated with ether to give the crude acid as an amorphous yellow solid. This was dissolved in saturated aqueous sodium hydrogen carbonate, filtered, and chromatographed on HP20SS eluting with 100ml portions of 0,2,4,6,8 and 10% THF/water. The fractions containing the product, monitored by h.p.l.c., were combined, concentrated and freeze-dried. The title compound was obtained as a yellow amorphous solid, (0.119 g, 55%), $\lambda_{max}$ (H$_2$O) 302 ($\epsilon$12570), and 212nm ($\epsilon$27685); $\nu_{max}$ (KBr) 1761, 1669, 1609, 1527 and 1382cm$^{-1}$; $\delta_H$ (d$_6$-DMSO) 3.86 (3H,s), 5.28 (1H,d,J4.9Hz), 5.70 (1H,dd,J4.9,8.1Hz), collapses to a d on D$_2$O shake, J4.9Hz), 6.75 (1H,s), 6.76 (1H,s), 7.26 (1H,br.s, exch), 7.64 (1H,m), 7.81 (2H,m), 7.92 (1H,d,J7.7Hz) and 9.65 (1H,d,J8.1Hz, exch.); [mass spectrum: +ve ion (thioglycerol) MH$^+$, 550, MNa$^+$, 572].

EXAMPLE 6

Sodium 7β-[2-(2-Aminothiazol-4-yl)-2-Z-methoxyiminoacetamido]-3-(E-2,5-dihydro-4-methyl-2-oxo-3-phenylfuran-5-ylidenemethyl)ceph-3-em-4-carboxylate (a) 5-Bromo-2,5-dihydro-4-methyl-2-oxo-3-phenylfuran 2,5-Dihydro-4-methyl-2-oxo-3-phenylfuran, (U.S. Pat. No. 3,622,569), (355 g) in carbon tetrachloride (50 mls) and N-bromosuccinimide (3.85 g) were heated under reflux in the presence of 2,2′-azobisisobutyronitrile (AIBN) (cat.quantity) and a 150W lamp. After 1 h a pale yellow solution was formed accompanied by the presence of succinimide. T.l.c. analysis showed a mixture of products. After filtration, and removal of solvent, the residue was purified by flash chroma-tography on silica gel eluting with 10% ethyl acetate/hexane. The title compound was obtained as a viscous yellow oil, (3.53 g, 68%), (Found; M+, 251.9802. $C_{11}H_9O_2Br$ requires M, 251.9786); $\nu_{max}$ 1780(s) and 1650(w)cm$^{-1}$; $\delta_H$ (CDCl$_3$) 2.28 (3H,s), 6.80 (1H,s) and 7.45 (5H,m).

(b)
2,5-Dihydro-4-methyl-2-oxo-3-phenylfuran-5-yl-triphenylphosphonium bromide

5-Bromo-2,5-dihydrofuran-4-methyl-2-oxo-3-phenylfuran (3.46 g) and triphenylphosphine (4.14 g) in benzene (50 mls), were heated under reflux overnight. The colourless salt was filtered off, washed with benzene, then ether (2 portions), and dried to give the title compound as a white solid, (6.13 g, 85%), m.p. 214°–217° C. (decomp), acetonitrile/ethyl acetate. (Found: C, 67.21; H, 4.61; Br, 15.65%. $C_{29}H_{24}BrO_2P$ requires C, 67.58; H, 4.69; Br, 15.51%); $\nu_{max}$ (CH$_2$Cl$_2$) 1775(s)cm$^{-1}$; $\delta_H$ (CDCl$_3$) 2.14 (3H,d,J4Hz), 7.1–8.5 (20H,m) and 9.75 (1H,d,J7Hz); [mass spectrum: +ve ion (thioglycerol) MH+, 435].

(c) Diphenylmethyl 3-(E-2,5-dihydro-4-methyl-2-oxo-3 phenylfuran-5-ylidenemethyl)-7β-phenylacetamidoceph-3-em-4-carboxylate 2,5-Dihydro-4-methyl-2-oxo-3-phenylfuran-5-yl-triphenylphosphonium bromide (2.21 g) and diphenylmethyl 3-formyl-7β-phenylacetamidoceph-3-em-4-carboxylate (2 g) in dichloromethane (30 mls) and saturated aqueous sodium hydrogen carbonate (30 mls) were stirred vigorously at room temperature for ca 20 mins. T.l.c. analysis showed all the starting material had been consumed. The organic layer was separated and washed with dilute hydrochloric acid, brine and then dried. After removal of solvent, the residue was flash chromatographed on silica gel eluting with 40% ethyl acetate/hexane. After trituration with ether, the title compound was obtained as a pale yellow crystalline compound, (0.643 g, 25%), m.p. 180°–183° C. (decomp.) ethyl acetate/hexane. (Found: C, 71.93; H, 5.10; N, 4.17; S, 4.54.%. $C_{40}H_{32}N_2O_6S$ requires C, 71.84; H, 4.82; N, 4.19; S, 4.79%); $\nu_{max}$ (CH$_2$Cl$_2$) 1785, 1760, 1715, 1680, 1490 and 1365cm$^-$; $\delta_H$ (CDCl$_3$) 1.99 (3H,s), 3.44 (2H,ABq, J18.7Hz), 3.67 (2H,ABq,J16.1Hz), 5.02 (1H,d,J4.9Hz), 5.93 (1H,dd,J4.9,8.9Hz), 6.08(1H,d,J8.9Hz), 6.28(1H,s), 6.97 (1H,s) and 7.1–7.5 (20H,m); [mass spectrum: +ve ion (3-NOBA, Na+) MNa+, 691].

(d) Diphenylmethyl 7β-Amino-3-(E-2,5-dihydro-4-methyl-2-oxo-3-phenylfuran-5-ylidenemethyl)ceph-3-em-4carboxylate Diphenylmethyl 3-(E-2,5-dihydro-4-methyl-2-oxo-3-phenylfuran-5-ylidenemethyl)-7β-phenylacetamidoceph-3-em-4-carboxylate (0.6 g) in dichloromethane (5 mls) under argon, was cooled to −20° C. N-methylmorpholine phosphorous pentachloride (0.253 g) in dichloromethane (6.075 mls). The solution was maintained at −20° C. for 30–40mins. I.r. analysis showed no starting material present Dry methanol (5 mls) was added rapidly, in one portion. The reaction mixture was allowed to warm to room temperature over 30mins. Water (10 mls) was then added and the solution vigorously stirred for 30 mins. The organic phase was separated, washed with brine and then dried. After removal of solvent the residue was purified by flash chromatography on silica gel, eluting with 70% ethyl acetate/hexane. The title compound was obtained as a yellow foam, (0.453 g, 92%), $\nu_{max}$ (CH$_2$Cl$_2$) 1780 (shoulder), 1760, 1720(w) and 1615(vw)cm$^{-1}$; $\delta_H$ (CDCl$_3$) 2.06 (3H,s), 3.47 (2H,ABq,J18.6Hz), 4.87 (1H,d,J5.1Hz), 5.00 (1H,d,J5.1Hz), 6.33 (1H,s), 7.00 (1H,s) and 7.1–7.5 (15H,m); [mass spectrum: +ve ion (3-NOBA, Na+) MNa+, 573].

(e) Diphenylmethyl 7β-[2-(2-Aminothiazol-4-yl)-2-Z-methoxyiminoacetamido[-3-(E-2,5-dihydro-4-methyl-2-oxo-3-phenylfuran-5-ylidenemethyl)ceph-3-em-4-carboxylate 2-(2-Aminothiazol-4-yl)-2-Z-methoxyiminoacetic acid (0.14 g) in dry DMF (2 mls), under argon was cooled to −50° C. To this was added diisopropylethylamine (0.158 mls) and then methanesulphonyl chloride (0.07 mls). The solution was maintained at −50° C. for 1 h, and then a solution of diphenylmethyl 7β-amino-3-(E-2,5-dihydro-4-methyl-2-oxo-3-phenylfuran-5-ylidenemethyl)ceph-3-em-4-carboxylate (0.416 g) and pyridine (0.061 mls) in dichloromethane (4 mls) was added in a rapid, dropwise fashion. The reaction mixture was allowed to warm slowly to room temperature, for ca 1 h. The solution was diluted with dichloromethane and washed with water, brine and then dried. Removal of solvent and flash chromatography on silica gel, eluting with 70% ethyl acetate/hexane, gave the title compound as a yellow foam, (0.408 g, 73%), $\nu_{max}$ (CH$_2$Cl$_2$) 3450(v.w), 3350(v.br), 1780 (shoulder), 1760(s), 1720(w), 1670(s), 1600(w), 1520 and 1370cm$^{-1}$; $\delta_H$ (CDCl$_3$) 2.03 (3H,s), 3.52 (2H,ABq,J18.7Hz), 4.08 (3H,s), 5.17 (1H,d,J5.0Hz), 5.41 (2H,s, exch.), 6.13 (1H,dd,J5.0,8.9Hz, collapses to a d on D$_2$O shake, J5.0Hz), 6.33 (1H,s), 6.84 (1H,s), 7.01 (1H,s), 7.1–7.5 (15H,m) and 7.76 (1H,d,J8.9Hz, exch.); [mass spectrum: +ve ion (3-NOBA, Na+), MNa+, 756].

(f) Sodium 7β-[2-(2-Aminothiazol-4-yl)-2-Z-methoxyiminoacetamido[-3-(E-2,5-dihydro-4-methyl-2-oxo-3-phenylfuran-5-ylidenemethyl)ceph-3-em-4-carboxylate Diphenylmethyl 7β-[2-(2-aminothiazol-4-yl)-2-Z-methoxyiminoacetamido]-3-(E-2,5-dihydro-4-methyl-2-oxo-3-phenylfuran-5-ylidenemethyl)ceph-3-em-4-carboxylate (0.386 g) was dissolved in trifluoroacetic acid (3 mls) at room temperature. After 5 mins the acid was removed in vacuo and the residue triturated with ether to give a yellow amorphous solid. This solid was dissolved in saturated aqueous sodium hydrogen carbonate and chromatographed on HP20SS, eluting with THF/water. The fractions containing the product as shown by h.p.l.c. were combined concentrated and freeze-dried. The title compound was obtained as a yellow solid, 0.122 g, 39%), $\nu_{max}$ (KBr) 1751, 1669, 1610, 1560, 1528, 1384, 1360 and 1307cm$^{-1}$; $\delta_H$ (d$_6$-DMSO) 2.23 (3H,s), 3.87 (3H,s), 3.93 (2H,ABq,J17.1Hz), 5.16 (1H,d,J5.0Hz), 5.68 (1H,dd,J5.0,8.1Hz, collapses to d on D$_2$O shake, J5.0Hz), 6.76 (1H,s), 7.10 (1H,s), 7.26 (2H,br.s, exch ), 7.4–7.6 (5H,m) and 9.64 (1H,d,J8.1Hz, exch.); [mass spectrum: +ve ion (thioglycerol), MH+, 590 and MNa+, 612].

EXAMPLE 7

7β-[2-(2-Aminothiazol-4-yl)-2-Z-hydroxyiminoacetamido]-3-(E-2,5-dihydro-3-methyl-2-oxofuran-5-ylidenemethyl)ceph-3-em-4-carboxylic acid (a) Diphenylmethyl 3-(E-2 5-dihydro-3-methyl-2-oxofuran-5-ylidenemethyl)-7β-[2-(2-triphenylmethyl aminothiazol-4-yl)-2-Z-triphenylmethoxyimino acetamido]ceph-3-em-4-carboxylate Sodium 2-(2-triphenylmethylaminothiazol-4-yl)2-Z-triphenylmethoxyiminoacetate (0.832 g), in dry DMF (2 mls) was cooled to ca −50° C. under argon and treated with methanesulphonyl chloride (0.093 mls). The solution was allowed to warm to −15° C. over 30mins and then treated with a solution of diphenylmethyl 7β-amino-3-(E-2,5-dihydro-3-methyl-2-oxofuran-5-ylidenemethyl)ceph-3-em-4-carboxylate (0.474 g) and pyridine (0.096 mls) in DMF (3 mls). The reaction was allowed to warm to room temperature over 1h., diluted with ethyl acetate and washed with water (3×), brine and dried. After removal of solvent, flash chromatography on silica gel eluting with 30, 40% ethyl acetate/hexane, gave the title compound as a foam, (0.444 g, 39%), $\nu_{max}$(CH$_2$Cl$_2$) 3375, 1780 (shoulder), 1760, 1720, 1680 and 1500cm$^{-1}$; $\delta_H$ (CDCl$_3$) 1.88 (3H,s), 3.37 (2H,ABq, J17.6Hz), 5.14 (1H,d,J5.1Hz), 6.10 (1H,dd,J5.1,8.8Hz), 6.44 (1H,s), 6.48 (1H,s) 6.77 (1H,br.s, exch.), 6.98 (1H,s), 7.00 (1H,s) and 7.2-7.4 (40H,m); [mass spectrum: +ve ion (NOBA) MH+, 1128].

(b)

7β-[2-(2-Aminothiazol-4-yl)-2-Z-hydroxyiminoacetamido[-3-(E-2,5-dihydro-3-methyl-2-oxofuran-5-ylidenemethyl)ceph-3-em-4-carboxylic acid Diphenylmethyl 3-(E-2,5-dihydro-3-methyl-2-oxofuran-5-ylidenemethyl)-7β-[2-(2-triphenylmethylaminothiazol-4-yl)-2-Z-triphenylmethoxyiminoacetamido]-ceph-3-em-4-carboxylate (0.855 g) was dissolved in 90% formic acid (5ml) and maintained at room temperature for 1 h, whereupon a crystalline precipitate was formed. Concentrated hydrochloric acid (0.2ml) was added, and reaction mixture left for a further 1 h. The solvent was removed in vacuo. The residue was shaken vigorously with water (30 mls) and ether (30 mls), filtered, washed with a little water and acetone and then dried. The title compound was obtained as a yellow solid, (0.258 g, 71%), $\nu_{max}$(KBr) 1741, 1669, 1629, 1540 and 1383cm$^{-1}$; $\delta_H$ (d$_6$-DMSO) 1.98 (3H,s), 3.89 (2H,ABq,J17.5z), 5.29 (1H,d,J5.0Hz), 5.86 (1H,dd,J5.0, 7.9Hz, collapses to a d on D$_2$O shake, J5.0Hz), 6.77 (1H,s), 6.81 (1H,s), 7.89 (1H,s), 8.11 (2H,v.br.s, exch.), 9.68 (1H,d,J7.9Hz, exch.) and 11.84 (1H,br.s, exch.); [mass spectrum: +ve ion (thioglycerol/acetic acid) MH+, 478].

EXAMPLE 8

Sodium 7β-[2-(2-Aminothiazol-4-yl)-2-Z-methoxyiminoacetamido-3-(E-2,5-dihydro-4-methoxy-3-methyl-2-oxofuran-5-ylidenemethyl)ceph-3-em-4-carboxylate (a) 2,5-Dihydro-5-hydroxy-4-methoxy-3-methyl-2-oxofuran 2-Methoxy-3-methylmaleic anhydride (9 g), (M. M. Kayser et al, Can.J.Chem., 1986, 64, 104) in dry THF (50 mls) was added, dropwise to a suspension of sodium borohydride (1.5 g) in THF (200 mls) at 0°-5° C., over ca 30 mins. The reaction mixture was allowed to warm to room temperature for a further 30 mins. T.l.c. analysis showed no remaining starting material. The solution was carefully neutralized with 5M aqueous hydrochloric acid and then the THF removed in vacuo. The aqueous solution was extracted with ethyl acetate washed with brine and dried. After removal of solvent the crude material was purified by 'flash' chromatography on silica gel eluting with 50% ethyl acetate/hexane. The title compound was obtained as a colourless crystalline solid, (6.683 g, 73%), m.p. 79° C., benzene. $\nu_{max}$ (CH$_2$Cl$_2$) 3540(w), 3300 (br), 1755, 1670, 1455, 1380 and 1325cm$^{-}$; $\delta_H$ (CDCl$_3$) 1.78 (3H, s), 4.06 (3H, s), 5.96 (1H, br.s, sharpens on D$_2$O shake) and 6.23 (1H, br.s, exch).

(b)

5-Bromo-2,5-dihydro-4-methoxy-3-methyl-2-oxofuran 2,5-Dihydro-5-hydroxy-4-methoxy-3-methyl-2-oxofuran (0.53 g) in dry diethyl ether (30 mls) was cooled to between 0°-5° C. (ice) and treated with pyridine (0.1 mls).

A solution of phosphorous tribromide in ether (10 mls) was then added dropwise over 10 mins, whereupon a white precipitate was formed. The reaction mixture was allowed to warm to room temperature and stir overnight. T.l.c. analysis showed complete conversion to the less polar product. The ether solution was washed with water, brine and then dried. Removal of solvent afforded the title compound as a sufficiently pure, colourless oil, $\nu_{max}$(CH$_2$Cl$_2$) 1780, 1665, 1450(w), 1395, 1340 and. 1295cm$^{-1}$; 1.94 (3H, s), 4.13 (3H, s) and 6.59 (1H, s).

(c)

2,5-Dihydro-4-methoxy-3-methyl-2-oxofuran-5-yl-triphenylphosphonium Bromide

5-Bromo-2,5-dihydro-4-methoxy-3-methyl-2-oxofuran (6.44 g) was dissolved in dry benzene (100 mls). Triphenylphosphine was added and the solution stirred overnight at room temperature. The solution was decanted from the orange gum, which was then triturated with ether to give a colourless crystalline solid. The ether was decanted and the salt dried under vacuum. The decanted solution was concentrated to a gum. Trituration of this with ether resulted in a second crop of the phosphonium salt. The combined crops gave the title compound as a colourless solid, (14 41 g, 99%), $\nu_{max}$ (CH$_2$Cl$_2$) 1775, 1665, 1435, 1390 and 1330cm$^{-1}$; $\delta_H$(CDCl$_3$) 1.74 (3H, m), 3.95 (3H, s) and 7.5-8.1 (16H, m); [mass spectrum: +ve ion (3NOBA, Na+) M+-Br, 389].

(d) Diphenylmethyl 3-(E and Z-2,5-dihydro-4-methoxy-3-methyl-2-oxofuran-5-ylidenemethyl)-7β-phenyl acetamidoceph-3-em-4-carboxylate Sodium hydride (0.094g, prewashed with n-hexane and dried), was dissolved in hot dimethyl sulphoxide (DMSO) under argon, to give a homogeneous grey-/green solution. A solution of 2,5-dihydro-4-methoxy-3-methyl-2-oxofuran-5-yltriphenylphosphonium bromide (1.83g) in DMSO (5 mls) was then added, and the resultant deep red/brown solution stirred at room temperature for 1 h. To this solution was added a solution of diphenylmethyl 3-formyl-7β-phenylacetamidoceph-3-em-4-carboxylate (2g) in DMSO (5 mls). The brown solution was stirred at room temperature for 30 mins. T.l.c. analysis showed the formation of two products. The solution was poured into water and extracted (2×) with ethyl acetate. The organic phase was washed with water, brine and then dried. After removal of the solvent in vacuo, the crude products were separated by 'flash' chromatography on silica gel, eluting with 5% ethyl acetate in dichloromethane. The first component to be eluted, crystallized from methanol and was subsequently shown to be the Z isomer (n.o.e) of the title compound, (0.333g; 14%); m.p. 186°–190° C., ethyl acetate/hexane, (Found: C, 67.26; H, 5.04; N, 4.33; S, 5.19%. $C_{35}H_{30}N_2O_7S$ requires C, 67.51; H, 4.86; N, 4.50; S, 5.15%); $\nu_{max}$ ($CH_2Cl_2$) 3400(w), 3340(vw), 1770(br), 1720, 1685, 1635, 1495, 1450(w), 1370 and 1345cm$^{-1}$; $\delta_H$ (CDCl$_3$) 2.08 (3H, s), 3.63 (2H, ABq, J16.0Hz), 3.93 (2H, ABq, J18.6Hz), 4.07 (3H, s), 4.97 (1H, d, J5.0Hz), 5.89 (1H, dd, J5.0, 9.3Hz), 6.22 (1H, d, J9 3Hz), 6.71 (1H, s), 6.94 (1H, s) and 7.2–7.5 (15H, m), [mass spectrum: +ve ion (3NOBA, Na$^+$) MNa$^+$, 645].

The second compound to be eluted was obtained as a yellow foam and shown to be the E isomer (n.o.e) of the title compound, (0.299 g, 12%), $\nu_{max}$ ($CH_2Cl_2$) 3400(w), 1785 (shoulder), 1765, 1720, 1680, 1635, 1495, 1370 and 1320cm$^{-1}$; $\delta_H$ (CDCl$_3$) 1.93 (3H, s), 3.41 (2H, ABq, J18.3Hz), 3.67 (2H, ABq, J16.2Hz), 3.83 (3H, s), 4.98 (1H, d, J5.8Hz), 5.87 (1H, dd, J5.8, 8.9Hz), 6.08 (1H, d, J8.9Hz), 6.21 (1H, s), 6.96 (1H, s) and 7.2–7.5 (15H, m); [mass spectrum: +ve ion (3NOBA, Na$^+$) MNa$^+$, 645].

(e) Diphenylmethyl 7β-Amino-3-(E-2,5-dihydro-4-methoxy-3-methyl-2-oxofuran-5-ylidenemethyl)ceph-3-em-4-carboxylate Diphenylmethyl 3-(E-2,5-dihydro-4-methoxy-3-methyl-2-oxofuran-5-ylidenemethyl)-7β-phenylacetamidoceph-3-em-4-carboxylate (0.47 g), in dry dichloromethane (5 mls) was cooled to −20° C. under argon. This was treated with N-methylmorpholine (0.183 mls) and then a solution of phosphorous pentachloride in dichloromethane (5.13 mls, 40 mgs/ml). The solution was maintained at −20° C. for 30 mins and then methanol (5 mls) was added quickly, in one portion. The solution was allowed to warm to room temperature for a further 30 mins and water (10 mls) added. The reaction was vigorously stirred for 30 mins and then the dichloromethane removed in vacuo. The pH was adjusted to 7–8 with aqueous saturated sodium hydrogen carbonate and then extracted with ethyl acetate. The organic layer was washed with brine, dried and concentrated. 'Flash' chromatography on silica gel, eluting with 80% ethyl acetate/hexane afforded the title compound as a yellow foam, (0.221 g, 58%), $\nu_{max}$ ($CH_2Cl_2$) 3400(vw), 1760, 1720, 1625, 1490(w) and 1450(w) cm$^{-1}$; $\delta_H$(CDCl$_3$) 1.94 (3H, s), 3.47 (2H, ABq, J18.2Hz), 3.87 (3H, s), 4.83 (1H, d, J5.1Hz), 4.98 (1H, d, J5.1Hz), 6.25 (1H, s), 7.00 (1H, s) and 7.2–7.5 (10H, m); [mass spectrum: +ve ion (3NOBA, Na$^+$) MNa$^+$, 527].

(f) Diphenylmethyl 7β-[2-(2-Aminothiazol-4-yl)-2-Z-methoxyiminoacetamido[-3-(E-2,5-dihydro-4-methoxy-3-methyl-2-oxofuran-5-ylidenemethyl)ceph-3-em-4carboxylate 2-(2-Aminothiazol-4-yl)-2-Z-methoxyiminoacetic acid (0.077 g) in dry DMF (2 mls) under argon was cooled to −50° C. and treated successively with diisopropylethylamine (0.086 mls) and methanesulphonyl chloride (0.038 mls) for 1 h. A solution of diphenylmethyl 7β-amino-3-(E-2,5-dihydro-4-methoxy-3-methyl-2-oxo-furan-5-ylidenemethyl)ceph-3-em-4-carboxylate (0.208 g) in dichloromethane (3 mls) and pyridine (0.033 mls) was added to the activated intermediate at −50° C. The solution was then allowed to warm to room temperature. The reaction mixture was diluted with dichloromethane and washed with water, brine and then dried. The solvent was removed and the residue purified by flash chromatography on silica gel eluting with ethyl acetate, to give the title compound as a pale yellow solid, (0.24 g, 85%), $\nu_{max}$ 3470(w), 3380(w), 3320(w), 1760, 1720, 1670, 1630, 1525, 1445(w), 1375 and 1315cm$^{-1}$; $\delta_H$(CDCl$_3$) 1.93(3H, s), 3.49 (2H, ABq, J16.1Hz), 3.84 (3H, s), 4.10 (3H, s), 5.13 (1H, d, J4.9Hz), 5.43 (1H, br.s, exch.), 6.10 (1H, dd, J4.9, [8.9Hz; collapses to d, J4.9Hz on D20 shake), 6.27 (1H, s), 6.86 (1H, s), 7.00 (1H, s), 7.25–7.4 (10H, m) and 7.67 (1H, d, J8.9Hz); [mass spectrum: +ve ion (3NOBA, Na$^+$) MNa$^+$710].

(g) Sodium 7β-[2-(2-Aminothiazol-4-yl)-2-Z-methoxyiminoacetamido[-3-(E-2,5-dihydro-4-methoxy-3-methyl-2-oxofuran-5-ylidenemethyl)ceph-3-em-4-carboxylate Diphenylmethyl 7β-[2-(2-aminothiazol-4-yl)-2-Z-methoxyiminoacetamido]-3-(E-2,5-dihydro-4-methoxy-3-methyl-2-oxofuran-5-ylidenemethyl)ceph-3-em-4-carboxylate (0.227 g) was dissolved in TFA (3 mls) at room temperature. After 8 mins the TFA was removed under vacuum, and toluene (5 mls) added, and subsequently evaporated. The oily residue was triturated with ether to give a pale yellow amorphous solid. This was dissolved in aqueous saturated sodium hydrogen carbonate, filtered through kieselguhr and chromatographed on HP20SS eluting with 0, 2, 4, 6 and 8% THF/water in 100ml portions. The fractions containing the product were combined, concentrated and freeze-dried to give the title compound as a yellow amorphous solid, (0.109 g, 61%), $\nu_{max}$ (KBr) 1751, 1670, 1624, 1529, 1455, 1385 and 1351cm$^{-1}$; $\delta_H$ (d$_6$ DMSO) 2.03 (3H, s), 3.58 (2H, ABq, 16.9Hz), 3.85 (3H, s), 4.14 (3H, s), 5.14 (2H, d, J5.0Hz), 5.63 (1H, dd, J5.0, 8.1Hz; collapses to d, J5.0Hz on D$_2$O shake), 6.74 (1H, s), 7.08 (1H, s), 7.26 (2H, br.s, exch.) and 9.61 (1H, d, J8.1Hz, exch.); [mass spectrum: +ve ion (thioglycerol) MH$^+$544, MNa$^+$566].

EXAMPLE 9

Sodium 7β-[2-(2-Aminothiazol-4-yl)-2-Z-methoxyiminoacetamido[-3-(Z-2,5-dihydro-4-methoxy-3-methyl-2-oxofuran-5-ylidenemethyl)ceph-3-em-4-carboxylate (a) Diphenylmethyl
7β-Amino-3-(Z-2,5-dihydro-4-methoxy-3-methyl-2-oxofuran-5-ylidenemethyl)ceph-3-em-4-carboxylate Diphenylmethyl 3-(Z-2,5-dihydro-4-methoxy-3-methyl-2-oxofuran-5-ylidenemethyl)-7β-phenylacetamidoceph-3-em-4-carboxylate (0.4 g) was treated with N-methylmorpholine (0.155 mls) and then phosphorous pentachloride (4.36 mls, 40 mg/ml solution in dichloromethane) as previously described in Example 8(e). Following work up the crude product was triturated with ether/ethyl acetate to give the title compound as a pale yellow solid containing about 20% of the unreacted starting material, (0.261 g, 81%), $\nu_{max}$ (CH$_2$Cl$_2$) 3400(vw), 1760, 1720, 1630, 1490(vw), 1445(w), 1385 and 1345cm$^{-1}$; $\delta_H$ (d$_6$ DMSO) 1.98 (3H, s), 3.90 (2H, ABq, J18.0Hz), 4.06 (3H, s), 4.89 (1H, br.d, J4.5Hz, sharpens to d, J5.2Hz on D$_2$O shake), 5.11 (1H, d, J5.2Hz), 6.28 (1H, s), 6.92 (1H, s) and 7.25–7.5 (10H, m); [mass spectrum: +ve ion (3NOBA, Na$^+$) MNa$^+$527].

(b) Diphenylmethyl
7β-[2-(2-Aminothiazol-4-yl)-2-Z-methoxyiminoacetamido[-3-(Z-2,5-dihydro-4-methoxy-3-methyl-2-oxofuran-5-ylidenemethyl)ceph-3-em-4-carboxylate 2-(2-Aminothiazol-4-yl)-2-Z-methoxyiminoacetic acid (0.093 g) was activated with methanesulphonyl chloride (0.047 mls) and diisopropylethylamine (0.105 mls) in DMF (2 mls) as described in Example 8(f). This was subsequently coupled to diphenylmethyl 7β-amino-3-(Z-2,5-dihydro-4-methoxy-3-methyl-2-oxofuran-5-ylidenemethyl)ceph-3-em-4-carboxylate (0.253 g) and pyridine (0.04 mls) in dichloromethane (5 mls). Purification by flash chromatography on silica gel eluting with 80% ethyl acetate/hexane afforded the title compound as a yellow solid (0.191 g, 55%), $\nu_{max}$ (CH$_2$Cl$_2$) 3475(w), 3380(w), 3320(w), 1760, 1720, 1675, 1630, 1525, 1445(w), 1370 and 1340cm$^{-1}$; $\delta_H$ (CDCl$_3$) 2.09 (3H, s), 4.03 (2H, ABq, J18.4Hz), 4.06 (3H, s), 4.11 (3H, s), 5.12 (1H, d, J4.9Hz), 5.62 (2H, br.s, exch.), 6.05 (1H, dd, J4.9, 9.0Hz, collapses to d, J4.9Hz on D$_2$O shake), 6.73 (1H, s), 6.90 (1H, s), 6.98 (1H, s),7.3–7.5 (10H, m) and 7.59 (1H, d, J9.0Hz); [mass spectrum: +ve ion (3NOBA, Na$^+$) MNa$^+$710].

(c) Sodium
7β-[2-(2-Aminothiazol-4-yl)-2-Z-methoxyiminoacetamido]-3-(Z-2,5-dihydro-4-methoxy-3-methyl-2-oxofuran-5-ylidenemethyl)ceph-3-em-4-carboxylate Diphenylmethyl 7β-[2-(2-aminothiazol-4-yl)-2-Z-methoxyiminoacetamido]-3-(Z-2,5-dihydro-4-methoxy-3-methyl-2-oxofuran-5-ylidenemethyl)ceph-3-em-4-carboxylate (0.168 g) was deprotected with TFA (2 mls) as described in Example 8(g). Following purification by HP20SS column chromatography the title compound was obtained as a pale yellow amorphous solid, (0.075 g, 57%), $\nu_{max}$(KBr) 1742, 1665, 1625, 1529, 1453, 1388 and 1356cm$^{-1}$; $\delta_H$ (d$_6$-DMSO) 2.02 (3H, s), 3.76 (2H, ABq, J17.2Hz), 3.85 (3H, s), 4.15 (3H, s), 5.09 (1H, d, J5.0Hz), 5.63 (1H, dd, J5.0, 8.2Hz, collapses to d, J5.0Hz on D$_2$O shake), 6.76 (2H, s, changes to 2s, at 6.68 and 6.77 on D$_2$O shake), 7.24 (2H, br. s, exch.) and 9.61 (1H, d, J8.2Hz, exch.); [mass spectrum: +ve ion (thioglycerol) MH$^+$-Na 522, MH$^+$544 and MNa$^+$566].

EXAMPLE 10

Sodium
7β-[2-(2-Aminothiazol-4-yl)-2-Z-methoxyimino acetamido]-3-(5RS)-2-oxotetrahydrofuran-5-yl methyl]ceph-3-em-4-carboxylate (a) Diphenylmethyl
3-[(5RS)-2-oxotetrahydrofuran-5-yl methyl]-7β-phenylacetamidoceph-3-em-4-carboxylate Diphenylmethyl 3-[(5RS)-2,5-dihydro-2-oxofuran-5-yl methyl]-7β-phenylacetamidoceph-3-em-4-carboxylate (Example 2(a)), (1.58 g) in 50% ethanol/benzene (100 mls) was treated with tris(triphenylphosphine)rhodium (I) chloride (0.75 g) and 10% palladium on carbon (0.2 g) and hydrogenated for several hours at room temperature. The reaction was monitored by t.l.c. analysis until formation of the slightly more polar product was complete. The solution was filtered through a small pad of silica gel and then concentrated. Purificationby 'flash' chromatography afforded the title compound as a brown solid, (0.62 g, 39%); a sample recrystallized from ethyl acetate was shown to be a single isomer by spectroscopic analysis, m.p. 84°–89° C., $\nu_{max}$ (KBr) 3400 (br), 3299, 1782, 1770, 1735, 1719, 1661, 1619, 1533, 1494, 1453 and 1373cm$^{-1}$; $\delta_H$ (CDCl$_3$) 1.75 (1H, m), 2.23 (2H, m), 2.43 (2H, m), 3.02 (1H, dd, J2.3, 13.8Hz), 3.52 (2H, ABq, J18.7Hz), 3.66 (2H, ABq, J16.2Hz), 4.66 (1H, m), 4.93 (1H, d, J4.7Hz), 5.87 (1H, dd, J4.7, 9.2Hz), 6.11 (1H, d, J9.2Hz), 6.84 (1H, s) and 7.25–7.5 (15H, m); [mass spectrum: +ve ion (3NOBA, Na$^+$) MNa$^+$605].

(b) Diphenylmethyl
7β-Amino-3-(5RS)-2-oxotetrahydrofuran-5-ylmethyl]-ceph-3-em-4-carboxylate Diphenylmethyl 3-[(5RS)-2-oxotetrahydrofuran-5-ylmethyl]-7β-phenylacetamidoceph-3-em-4-carboxylate, (0.62 g) in dichloromethane (5 mls) was treated with N-methylmorpholine (0.257 g) and phosphorous pentachloride (7.2 mls, 40 mgs/ml solution in dichloromethane), as described in Example 8(e). Purification by flash chromatography on silica gel eluting with 80% ethyl acetate/hexane afforded the title compound as a brown foam, (0.24 g, 49%), $\delta_H$ (CDCl$_3$) major isomer 1.74 (1H, m), 2.17 (1H, m), 2.3–2.5 (3H, m), 2.95 (1H, dd, J2.7, 13.9Hz), 3.56 (2H, ABq, J18.4Hz), 4.67 (1H, m), 4.77 (1H, d, J5.0Hz), 4.93 (1H, d, J5.0Hz), 6.88 (1H, s) and 7.25–7.5 (10H, m); [mass spectrum: +ve ion (3NOBA, Na$^+$) MNa$^+$487].

(c) Diphenylmethyl
3-[(5RS)-2-Oxotetrahydrofuran-5-ylmethyl]-7β-[2-(2-tritylaminothiazol-4-yl)-2-Z-methoxyiminoacetamido]-ceph-3-em-4-carboxylate 2-(2-Tritylaminothiazol-4-yl)-2-Z-methoxyiminoacetic acid hydrochloride, (0.257 g) was activated with methanesulphonyl chloride (0.042 mls) and diisopropylethylamine (0.186 mls) as previously described in Example 8(f).

This was treated with diphenylmethyl 7β-amino-3-[(5RS)-2-oxotetrahydrofuran-5-ylmethyl]ceph-3-em-4-carboxylate (0.266 g) and pyridine (0.039 mls) in dichloromethane (2 mls) in the prescribed manner and then warmed to 0° C. Following work up, flash chromatography on silica gel, eluting with 50 and then 60% ethyl acetate/hexane afforded the title compound as a colourless solid, (0.242 g, 56%), $\nu_{max}$ (CH$_2$Cl$_2$) 3380(w), 1780, 1720, 1680, 1510 and 1365cm$^{-1}$; $\delta_H$ (CDCl$_3$) major isomer 1.77 (1H, m), 2.2–2.5 (4H, m), 3.03 (1H, dd, J2.2, 13.7Hz), 3.58 (2H, ABq, J18.7Hz), 4.09 (3H, s), 4.68 (1H, m), 5.04 (1H, d, J4.8Hz), 5.96 (1H, dd, J4.8, 8.9Hz, collapses to d, J4.8Hz on D$_2$O shake), 6.76 (1H, s), 6.80 (1H, d, J8.9Hz, exch.), 6.86 (1H, s), 7.03 (2H, br.s, exch.) and 7.25–7.5 (25H, m); [mass spectrum: +ve ion (3NOBA, Na+) MNa+912]

(d) Sodium 7β-[2-(2-Aminothiazol-4-yl)-2-Z-methoxy iminoacetamido]-3-[(5RS)-2-oxotetrahydrofuran-5-yl methyl]ceph-3-em-4-carboxylate Diphenylmethyl 3-[(5RS)-2-oxotetrahydrofuran-5-yl methyl]-7β-[2-(2-tritylaminothiazol-4-yl)-2-Z-methoxyiminoacetamido]ceph-3-em-4-carboxylate (0.212 g) was deprotected with TFA (3 mls) as described in Example 8(g). Following purification by HP20SS column chromatography the title compound was obtained as a colourless, amorphous solid, (0.069 g, 58%), $\nu_{max}$(KBr) 1757, 1671, 1603, 1529, 1457(w), 1362 and 1289cm$^{-1}$; $\delta_H$(d$_6$-DMSO) major isomer 2.0–2.2 (2H, m), 2.47 (3H, m), 2.84 (1H, dd, J5.3, 13.3Hz), 3.35 (2H, ABq, J17.5Hz), 3.84 (3H, s), 4.80 (1H, m), 4.97 (1H, d, J4.7Hz), 5.53 (1H, dd, J4.7, 8.2Hz), 6.74 (1H, s), 7.26 (2H, br.s, exch.) and 9 53 (1H, d, J8.2Hz, exch.); minor isomer inter alia 1.8–2.0 (1H, m), 4.65 (1H, m) and 4.98 (1H, d, J4.5Hz); [mass spectrum: +ve ion (thioglycerol) MH+504, Na+526].

EXAMPLE 11

7β-[2-(2-Aminothiazol-4-yl)-2-Z-hydroxyiminoacetamido]-3-(Z-2,5-dihydro-4-methoxy-3-methyl-2-oxofuran-5-ylidenemethyl)ceph-3-em-4-carboxylic Acid (a) Diphenylmethyl 3-(Z-2,5-dihydro-4-methoxy-3-methyl-2-oxofuran-5-ylidenemethyl)-7β-2-(2-tritylaminothiazol-4-yl)-2-Z-trityloxyiminoacetamido]ceph-3-em-4-carboxylate Sodium 2-(2-tritylaminothiazol-4-yl)-2-Z-trityloxyiminoacetate (0.759 g), in dry DMF (5 mls) was cooled to ca −50° C. under argon. This solution was treated with methanesulphonyl chloride (0.085 mls) and allowed to warm to −15° C. A solution of diphenylmethyl 7β-amino-3-(Z-2,5-dihydro-4-methoxy-3-methyl-2-oxofuran-5-ylidenemethyl)ceph-3-em-4-carboxylate, (0.46 g) in dry DMF (5 mls) was added, and the solution allowed to reach room temperature over 1 h. The solution was diluted with ethl acetate and washed with water, brine and then dried. After removal of solvent the residue was flash chromatographed on silica gel eluting with 50% ethyl acetate/hexane to give the title compound as a yellow foam, (0.375 g, 36%), $\nu_{max}$ 3380, 1770(br), 1725, 1685, 1630, 1505(br), 1440, 1370 and 1345cm$^{-1}$; $\delta_H$ (CDCl$_3$) 2.07 (3H,s), 3.74 and 3.96 (2H,ABq, J18.3Hz, sharpens on D$_2$O shake), 5.08 (1H, m, sharpens to d, J5.0Hz on D$_2$O shake), 6.12 (1H, br.m, sharpens to d, J5.0Hz on D$_2$O shake), 6.43 (1H, br.s, sharpens on D$_2$O shake), 6.74 (1H, s), 6.78 (1H, br.s, exch.), 6.98 (1H, s) and 7.20 to 7.55 (40H, m, arom-H); [mass spectrum: +ve ion (NOBA, Na+) MNa+, 1180].

(b) 7β-[2-(2-Aminothiazol-4-yl)-2-Z-hydroxyiminoacetamido[-3-(Z-2,5-dihydro-4-methoxy-3-methyl-2-oxofuran-5-ylidenemethyl)ceph-3-em-4-carboxylic Acid Diphenylmethyl 3-(Z-2,5-dihydro-4-methoxy-3-methyl-2-oxofuran-5-ylidenemethyl)-7β-[2-(2-tritylaminothiazol-4-yl)-2-Z-trityloxyiminoacetamido]-ceph-3-em-4-carboxylate, (0.35 g) was dissolved in 98% formic acid (2.7 mls) containing 1M hydrochloric acid (0.3 mls) at ambient temperature. After ca 5 mins a colourless crystalline precipitate was formed. After 1 h conc. hydrochloric acid (1 drop) was added and the reaction mixture left for a further 30 mins. The solution/solid was filtered and the solid washed with a little 10% hydrochloric acid in formic acid, and then water. The filtrate was evaporated under reduced pressure. The residue was diluted with water and the pH adjusted to 3 with 0.1M sodium hydroxide. The pale yellow solid was filtered off and washed with small amounts of water, methanol and then diethyl ether. After drying, the residue was vigorously stirred in ethyl acetate (1 ml) overnight. After filtering and drying, the title compound was obtained as a pale yellow solid, (0.017 g, 46%), $\nu_{max}$(KBr) 1751(br), 1670 (shoulder), 1630, 1526, 1451, 1389 and 1353cm$^{-1}$; $\delta_H$(d$_6$-DMSO) 2.06 (3H, s), 3.87 and 4.00 (2H, ABq, J17.8Hz), 4.19 (3H, s), 5.24 (1H, d, J5.0Hz), 5.86 (1H, dd, J4.9, 8.2Hz, collapses to d, J4.9Hz on D$_2$O shake), 6.49 (1H. s), 6.68 (1H. s), 7.15 (2H, br.s, exch.), 9.49 (1H, d, J8.2Hz, exch.) and 11.33 (1H, s, exch.); [mass spectrum: +ve ion (thioglycerol) MH+508].

EXAMPLE 12

7β-[2-(2-Aminothiazol-4-yl)-2-Z-hydroxyiminoacetamido]-3-(2,5-dihydro-2-oxofuran-5-ylmethyl)ceph-3-em-4-carboxylic acid.

(a) Diphenylmethyl 3-(2,5-dihydro-2-oxofuran-5-yl-methyl)-7β-2-(2-triphenylmethylaminothiazol-4-yl)-2-Z-triphenylmethoxyiminoacetamido]ceph-3-em-4-carboxylate.

Sodium 2-(2-triphenylmethylaminothiazol-4-yl)-2-Z-triphenylmethoxyiminoacetate (1.33 g) in DMF (5 mls) was activated with methanesulphonyl chloride (0.148 mls) as described in example 7(a). Treatment with diphenylmethyl 7β-amino-3-[(5RS)-2,5-dihydro-2-oxofuran-5-ylmethyl]ceph-3-em-4-carboxylate (0.737 g) in DMF (5 mls), work up and purification by repeated flash, silica gel chromatography afforded major isomer of the title compound, (0.614 g, 35%), $\nu_{max}$ 3380(w), 1785, 1770 (shoulder), 1755 (shoulder), 1725, 1685, 1510 and 1370cm$^{-1}$; $\delta_H$(CDCl$_3$) 2.25 (1H, dd, J 9.9, 13.7Hz), 3.16 (1H, dd, J 2.9, 13.7Hz), 3.49 and 3.53 (2H, ABq, J 18.7Hz), 5.03 (1H, d, J 4.9Hz), 5.22 (1H, J 7.9Hz), 6.05 (1H, dd, J 1.9, 5.7Hz), 6.14 (1H, dd, J 4.9, 9.1Hz), 6.45 (1H, s), 6.76 (1H, broad s, exch.), 6.90 (1H, s), 7.07 (1H, d, J 9.1Hz, exch.), 7.19 (1H, dd, J 1.4, 5.7Hz) and 7.24 to 7.50 (40H, m); [mass spectrum: +ve ion (NOBA, Na+) MNa+1138]. The minor isomer was not progressed.

(b) 7β-2-(2-Aminothiazol-4-yl)-2-Z-hydroxyiminoacetamido]-3-(2,5-dihydro-2-oxofuran-5-ylmethyl)ceph-3-em-4-carboxylic acid.

Diphenylmethyl 3-(2,5-dihydro-2-oxofuran-5-ylmethyl)-7β-[2-(2-triphenylmethylaminothiazol-4-yl)-2-Z-triphenylmethoxyiminoacetamido]ceph-3-em-4-carboxylate, (0.375 g) was dissolved in a solution of 10% conc. hydrochloric acid in 98% formic acid (3 mls). Within a few minutes a colourless crystalline precipitate had formed. The solution was maintained at room temperature for 45 mins and then filtered. The solid was washed with a little 10% conc. hydrochloric acid/formic acid and then water. The solvent was removed from the filtrate in vacuo and the residue partitioned between water and ether (5 mls). The aqueous phase was adjusted to pH 3 and filtered. The yellow homogeneous solution was chromatographed on HP20SS, eluting with 2,4,6,8 and 10% THF/water (100ml portions). The fractions containing the product were combined, concentrated and freeze-dried to give the title compound as an amorphous white solid, (0.037 g, 24%), $\nu_{max}$(KBr) 1751 (v.broad), 1670, 1629, 1529, 1363, 1262 and 1178cm$^{-1}$; 2.84 (1H, dd, J 4.6, 14.5Hz), 2.94 (1H, dd, J 7.5, 14.5Hz), 3.38 and 3.59 (2H, ABq, J 17.6Hz), 5.17 (1H, d, J 4.7Hz), 5.44 (1H, m), 5.73 (1H, d, J 4.7Hz), 6.16 (1H, dd, J 1.9, 5.8Hz), 7.06 (1H, s) and 7.70 (1H, dd, J 1.1, 5.8Hz); [mass spectrum: +ve ion (thioglycerol) MH+466, MNa+488].

EXAMPLE 13

Sodium
7β-[2-(2-Aminothiazol-4-yl)-2-Z-methoxyiminoacetamido]-3-(E-2-oxotetrahydrofuran-3-ylidenemethyl) ceph-3-em-4-carboxylate.

(a) 2-Oxotetrahydrofuran-3-yltriphenylphosphonium bromide.

3-Bromo-2-oxotetrahydrofuran (5 g) and triphenylphosphine (7.94 g) in dry benzene (50 mls) were left at room temperature for 4 days. The solution was decanted from the orange gum. This was dissolved in dichloromethane and concentrated to give a pale brown foam.

(b)
2-Oxotetrahydrofuran-3-ylidenetriphenylphosphorane.

2-Oxotetrahydrofuran-3-yltriphenylphosphonium bromide (1.717 g) was dissolved in water (20 mls) and the solution filtered through kieselguhr. The pH was adjusted to 7.5 with 5M sodium hydroxide. The greyish precipitate was filtered off, washed with 50% ether/acetone and dried, to give the title compound as an off white solid, (0.77 g, 55%), (Found; M+, 346.1124. $C_{22}H_{19}O_2P$ requires M, 346.1123); $\nu_{max}$ (CH$_2$Cl$_2$) 1645, 1480(w), 1430(w), 1365(w) and 1315(w)cm$^{-1}$; $\delta_H$ (CDCl$_3$) 2.62 (2H, t, 7Hz), 4.27 (2H, t, J 7Hz) and 7.3–7.9 (15H, m).

(c) Diphenylmethyl
7B-Phenylacetamido-3-(E-2-oxotetrahydrofuran-3-ylidenemethyl)ceph-2-em-4-carboxylate.

Diphenylmethyl 3-formyl-7β-phenylacetamidoceph-2-em-4-carboxylate (0.45 g), (British patent no. 1,342,241; 1974), and the phosphorane prepared in example 13(c), (0.333 g) in dichloromethane (10 mls) were maintained at room temperature over 2 days. The solution was concentrated and flash chromatographed on fine silica gel, eluting with 40,50 and 60% ethyl acetate/hexane. The title compound was obtained as a colourless amorphous solid, (0.461 g, 90%), m.p. 169°–171° C. (ethyl acetate), (Found: C, 68.28; H, 4.65, N, 4.89; S, 5.37%. $C_{33}H_{28}N_2O_6S$ requires C, 68.26; H, 4.86; 4.82; S, 5.52%); $V_{max}$ (CH$_2$Cl$_2$ 3420(w), 1780, 1745, 1680, 1630(w) and 1490cm$^{-1}$; $\delta_H$ (CDCl$_3$) 2.68–3.02 (2H, m), 3.65 (2H, s), 4.14 (2H, m), 5.25 (1H, d, J 4.0Hz), 5.26 (1H, s), 5.59 (1H, dd, J 4.0, 8.3Hz), 6.34 (1H, d, J 8.3Hz), 664 (1H, s), 6.87 (1H, s), 7.01 (1H, t, J 2.6Hz) and 7.2–7.4 (15H, m); [mass spectrum: +ve ion (3NOBA, Na+) MNa+603].

(d) Diphenylmethyl
7β-Phenylacetamido-3-(E-2-oxotetrahydrofuran-3-ylidenemethyl)ceph-3-em-4-carboxylate.

The −2 isomer prepared in example 13(c) (0.848 g), was dissolved in dichloromethane (20 mls) cooled to 0°–5° C. and treated with m-chloroperbenzoic acid, (0.327 g, 85% pure). After 30 mins t.l.c. analysis showed no starting material. The solution was diluted with dichloromethane and washed with aqueous sodium bisulphite, sodium hydrogen carbonate and brine. After drying and removal of solvent, the crude sulphoxide was obtained as a white crystalline solid. This product was dissolved in dry DMF (5 mls), cooled to ca −30° C. under argon and treated with phosphorous trichloride (0.4 g) for 15–30 mins, until t.l.c. showed completion of the reaction. The solution was poured in water and extracted with portions of ethyl acetate, dried and concentrated. Trituration with ether gave the title compound as a pale yellow amorphous solid, (0.437 g, 52%), $\nu_{max}$(KBr) 1775, 1757, 1728, 1669, 1527, 1493, 1451 and 1380cm$^{-1}$; $\delta_H$(d$_6$-DMSO) 2.9–3.1 (1H, m), 3.2–3.3 (1H, m), 3.50 and 3.58 (2H, ABq, J 13.8Hz), 3.89 and 4.00 (2H, ABq,J 17.7Hz), 4.20–4.37 (2H, m), 5.22 (1H, d, J 5.1Hz), 5.86 (1H, dd, J 5.1, 8.3Hz), 6.98 (1H, s), 7.2–7.6 (15H, m) and 9.25 (1H, d, J 8.3Hz); [mass spectrum: +ve ion (3NOBA, Na+) MNa+603].

(e) Diphenylmethyl
7β-Amino-3-(E-2-oxotetrahydrofuran-3-ylidenemethyl)ceph-3-em-4-carboxylate.

Diphenylmethyl 7β-phenylacetamido-3-[E-2-oxotetrahydrofuran-3-ylidenemethyl)ceph-3-em-4-carboxylate, (0.38 g) in dry dichloromethane (3 mls), cooled to −20° C. under argon, was treated with N-methylmorpholine (0.146 g, 0.158 mls) and a solution of phosphorous trichloride (0.178 g) in dichloromethane (4.4 mls). After 30 mins at −20° C., methanol (5 mls) was added rapidly in one portion. The reaction mixture was allowed to warm slowly to room temperature over 30 mins, and then water (10 mls) added. After vigorous stirring for a further 30 mins the solvents were completely removed in vacuo. The residue was partitioned between ethyl acetate/hexane after adjusting the pH to 8 using aqueous 0.880 ammonia. After washing and drying the organic layer, the solvent was removed and the crude product triturated with ether. Flash chromatography on fine silica gel eluting with ethyl acetate afforded the title compound as a pale yellow foam, (0.116 g, 39%), $\nu_{max}$ (CH$_2$Cl$_2$) 1780, 1750 and 1720cm$^{-1}$; $\delta_H$ (CDCl$_3$) 2.57–2.72 (1H, m), 2.80–2.96 (1H, m), 3.61 (2H, s), 4.07–4.26 (2H, m), 4.85 (1H, d, J 5.1Hz), 4.98 (1.1Hz), 4.98 (1H, d, J 5.1Hz), 7.04 (1Hz), 7.04 (1H, s) and 7.2–7.5 (10H, m); [mass spectrum: +ve ion (3NOBA, Na+) MNa+485].

(f) Diphenylmethyl
3-(E-2-Oxotetrahydrofuran-3-ylidenemethyl)-7β-2-(2-triphenylmethylaminothiazol-4-yl)-2-Z-methoxyiminoacetamido1ceph-3-em-4-carboxylate.

2-(2-Triphenylmethylaminothiazol-4-yl)-2-Z-methoxyiminoacetic acid hydrochloride (0.114 g) was activated with diisopropylethylamine (0.061 g, 0.083 mls) and methanesulphonyl chloride (0.027, 0.019 mls) in DMF (2 mls) as described in example 8(f). To the activated ester was added diphenylmethyl 7β-amino-3-(E-2-oxotetrahydrofuran-3-ylidenemethyl)ceph-3-em-4-carboxylate (0.1 g) and pyridine (0.017 g, 0.018 mls) in dichloromethane (2 mls), in the presribed manner. Following the same work up, and purification by flash silica gel chromatography the title compound was obtained as a colourless, amorphous solid, (0.114 g, 59%), $\nu_{max}$ (CH$_2$Cl$_2$) 3380, 1785, 1750, 1720, 1680 and 1510cm$^{-1}$; $\delta_H$ (CDCl$_3$) 2.54–2.70 (1H, m), 2.76–2.95 (1H, m), 3.59 (2H, s), 4.08–4.28 (5H, s, overlapping m), 5.10 (1H, d, J 4.9Hz), 5.99 (1H, dd, J 4.9, 8.7Hz, collapses to d, J 4.9Hz on D$_2$O shake), 6.76 (1H, s), 6.82 (1H, d, J 8.7Hz, exch. on D$_2$O shake), 7.03 (1H, s) and 7.2–7.5 (25H, m); [mass spectrum: +ve ion (3NOBA, Na+) MNa+910].

(g) Sodium 7β-[2-(2-Aminothiazol-4-yl)-2-Z-methoxyiminoacetamido]-3-(E-2-oxotetrahydrofuran-3-ylidenemethyl)ceph-3-em-4-carboxylate.

Diphenylmethyl 3-(E-2-oxotetrahydrofuran-3-ylidenemethyl)- 7β-[2-(2-triphenylmethylaminothiazol-4-yl)-2-Z-methoxyiminoacetamido]ceph-3-em-4-carboxylate (0.105 g) was deprotected with TFA (2 mls) as described in example 8(g). Purification of the crude material with HP20SS column chromatography afforded the title compound as an amorphous white solid, (0.035 g, 59%), $\nu_{max}$(KBr) 1770, 1670, 1617, 1529, 1387, 1342 and 1206cm$^{-1}$; $\delta_H$ (d$_6$-DMSO) 3.0–3.15 (1H, m), 3.2–3.35 (1H, m), 3.70 and 3.78 (2H, ABq, J 16.6Hz), 3.84 (3H, s), 4.15–4.35 (2H, m), 5.06 (1H, d, J 5.0Hz), 5.16 (1H, dd, J 5.0, 8.0Hz collapses to d, J 5.0Hz on D$_2$O shake), 6.74 (1H, s), 7.26 (2H, s, exch.), 7.63 (1H, s) and 9.64 (1H, d, J 8.0Hz, exch.); [mass spectrum: +ve ion (3NOBA, Na+) MH+524].

In Vitro Biological Data

MIC (ug/ml)

| Example No. | Organism | |
|---|---|---|
| | E.coli (NCTC 10418) | S.aureus (Oxford) |
| 1 | <0.03 | 1.0 |
| 2 | 0.06 | 1.0 |
| 5 | 0.12 | 16.0 |
| 6 | 4.0 | 4.0 |
| 7 | 4.0 | 64.0 |
| 8 | <0.03 | 1.0 |
| 9 | 0.03 | 0.5 |
| 10 | 0.25 | 1.0 |
| 11 | 2.0 | 4.0 |
| 12 | 0.25 | 0.25 |
| 13 | <0.06 | 2.0 |

We claim:

1. A compound of formula (I) or a pharmaceutically acceptable salt thereof;

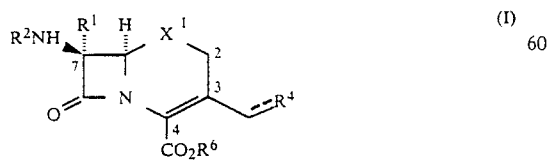

wherein
R$^1$ is hydrogen, methoxy or formamido;
R$^2$ is acyl;
CO$_2$R$^3$ is carboxy or a carboxylate anion, or R$^3$ is a readily removable carboxy protecting group; R$^4$ is a butenolide or butanolide ring, unsubstituted or substituted by one or two moieties selected from the group consisting of alkyl of 1 to 6 carbon atoms, dialkylamino of 1 to 6 carbon atoms in each alkyl moiety, alkoxy of 1 to 6 carbon atoms, hydroxy, halogen and aryl, wherein the aryl moiety is phenyl or naphthyl, unsubstituted or substituted with up to five substituents selected from the group consisting of halogen, mercapto, alkyl of 1 to 6 carbon atoms, phenyl, alkoxy of 1 to 6 carbon atoms, hydroxyalkyl of 1 to 6 carbon atoms, mercaptoalkyl of 1 to 6 carbon atoms, haloalkyl of 1 to 6 carbon atoms, hydroxy, amino, nitro, carboxy, alkylcarbonyloxy of 1 to 6 carbon atoms in the alkyl moiety, alkoxycarbonyl of 1 to 6 carbon atoms in the alkoxy moiety, formyl and alkylcarbonyl of 1 to 6 carbon atoms in the alkyl moiety, which may be the same or different, or, wherein two adjacent carbon atoms which are available for substitution define the common bond of phthalidyl unsubstituted or mono- or di- substituted with one or two substituents selected from the group consisting of alkyl of 1 to 6 carbon atoms, alkoxy of 1 to 6 carbon atoms, phenyl and naphthyl, said phenyl or naphthyl being unsubstituted or substituted with up to five substituents selected from the group consisting of halogen, mercapto, alkyl of 1 to 6 carbon atoms, phenyl, alkoxy of 1 to 6 carbon atoms, hydroxyalkyl of 1 to 6 carbon atoms, mercaptoalkyl of 1 to 6 carbon atoms, haloalkyl of 1 to 6 carbon atoms, hydroxy, amino, nitro, carboxy, alkylcarbonyloxy of 1 to 6 carbon atoms in the alkyl moiety, alkoxycarbonyl of 1 to 6 carbon atoms in the alkoxy moiety, formyl and alkylcarbonyl of 1 to 6 carbon atoms in the alkyl moiety;
X is S, SO or SO$_2$; and the dashed line adjacent to R$^4$ is an optional double bond.

2. A compound according to claim 1 in which R$^2$ is acyl of the formula (a) to (f):

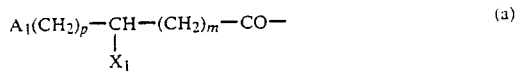

wherein p is 0, 1 or 2, m is 0, 1 or 2; A$_1$ is unsubstituted or substituted alkyl of 1 to 6 carbon atoms, cycloalkyl of 3 to 6 carbon atoms, cyclohexyl, cyclohexadienyl, aromatic phenyl unsubstituted or substituted by phenyl, thienyl, pyridyl, or unsubstituted or substituted by up to three substituents selected from the group consisting of halogen, alkyl of 1 to 6 carbon atoms, alkoxy of 1 to 6 carbon atoms haloalkyl of 1 to 6 carbon atoms, hydroxy and carboxy or a pharmaceutically acceptable salt or in vivo hydrolysable ester thereof, phenyl, naphthyl and oxo, alkylthio of 1 to 6 carbon atoms or alkyloxy of 1 to 6 carbon atoms; $X_1$ is hydrogen, halogen, carboxylic acid or an in vivo hydrolysable ester thereof, sulphonic acid, azido, tetrazolyl, hydroxy, acyloxy, amino, ureido, acylamino wherein the acyl is selected from the group consisting of alkanoyl of 1 to 6 carbon atoms, benzoyl, trichloroethoxycarbonyl and chloroacetyl, heterocyclylamino of 4- to 7-ring members having up to four hetero-atoms in each ring selected from the group consisting of oxygen, nitrogen and sulphur, unsubstituted or substituted by up to three substituents selected from the group consisting of halogen, alkyl of 1 to 6 carbon atoms, alkoxy of 1 to 6 carbon atoms, haloalkyl of 1 to 6 carbon atoms, hydroxy, carboxy, pharmaceutically acceptable salts and in vivo hydrolysable esters, guanidino or acylureido wherein the acyl is selected from the group consisting of alkanoyl of 1 to 6 carbon atoms, benzoyl, trichloroethoxycarbonyl and chloroacetyl; $A_2$ is phenyl, 2,6-dimethoxyphenyl, 2-alkoxy-1-naphthyl, 3-arylisoxazolyl, or 3-aryl-5-methylisoxazolyl wherein the aryl moiety is unsubstituted or substituted phenyl or naphthyl with up to five substituents selected from the group consisting of halogen, mercapto, alkyl of 1 to 6 carbon atoms, phenyl, alkoxy of 1 to 6 carbon atoms, hydroxyalkyl of 1 to 6 carbon atoms, mercaptoalkyl of 1 to 6 carbon atoms, haloalkyl of 1 to 6 carbon atoms, hydroxy, amino, nitro, carboxy, alkylcarbonyloxy of 1 to 6 carbon atoms in the alkyl moiety, alkoxycarbonyl of 1 to 6 carbon atoms in the alkoxy moiety, formyl and alkylcarbonyl of 1 to 6 carbon atoms in the alkyl moiety; substituted alkyl of 1 to 6 carbon atoms; or dithietane substituted by up to three substituents selected from the group consisting of halogen, alkyl of 1 to 6 carbon atoms, alkoxy of 1 to 6 carbon atoms, haloalkyl of 1 to 6 carbon atoms, hydroxy and carboxy or a pharmaceutically acceptable salt or in vivo hydrolysable ester thereof, phenyl, naphthyl and oxo; $X_2$ is $CH_2OCH_2$, $CH_2SCH_2$ or alkylene; $X_3$ is oxygen or sulphur; $A_3$ is unsubstituted or substituted phenyl or amino thiazolyl in which the amino group is protected or not protected; and $A_4$ is hydrogen, alkyl of 1 to 6 carbon atoms, cycloalkyl of 3 to 8 carbon atoms, alkoxycarbonyl alkyl of 1 to 6 carbon atoms in each alkyl moiety, alkenyl of 2 to 6 carbon atoms, carboxy alkyl of 1 to 6 carbon atoms, alkynyl of 2 to 6 carbon atoms, aryl and aryl alkyl of 1 to 6 carbon atoms; wherein the aryl moiety is phenyl or naphthyl, unsubstituted or substituted with up to five substituents selected from the group consisting of halogen, mercapto, alkyl of 1 to 6 carbon atoms, phenyl, alkoxy of 1 to 6 carbon atoms, hydroxyalkyl of 1 to 6 carbon atoms, mercaptoalkyl of 1 to 6 carbon atoms, haloalkyl of 1 to 6 carbon atoms, hydroxy, amino, nitro, carboxy, alkylcarbonyloxy of 1 to 6 carbon atoms in the alkyl moiety, alkoxycarbonyl of 1 to 6 carbon atoms in the alkoxy moiety, formyl and alkylcarbonyl of 1 to 6 carbon atoms in the alkyl moiety wherein the substituents for phenyl or naphthyl are up to 5 substituents selected from the group consisting of halogen, mercapto, alkyl of 1 to 6 carbon atoms, phenyl, alkoxy of 1 to 6 carbon atoms, hydroxyalkyl of 1 to 6 carbon atoms, mercaptoalkyl of 1 to 6 carbon atoms, haloalkyl of 1 to 6 carbon atoms, hydroxy, amino, nitro, carboxy, alkylcarbonyloxy of 1 to 6 carbon atoms in the alkyl moiety, alkoxycarbonyl of 1 to 6 carbon atoms in the alkyl moiety, formyl and alkylcarbonyl of 1 to 6 carbon atoms in the alkyl moiety.

3. A compound according to claim 2, in which $R^2$ is acyl of the formula (a) wherein $A_1$ is phenyl, $X_1$ is hydrogen and p and m are O; or $R^2$ is acyl of the formula (e) wherein $A_3$ is 2-aminothiazol-4-yl or 2-tritylaminothiazol-4-yl and $A_4$ is hydrogen, methyl, or triphenylmethyl.

4. A compound according to claim 1 in which $R^1$ is hydrogen; $R^2$ is 2-(2-aminothiazol-4-yl)-2-Z-methoxyiminoacetic or 2-(2-aminothiazol-4-yl)-2-Z-hydroxyiminoacetyl; $CO_2R^3$ is carboxy or a carboxylate anion, or $R^3$ is pivaloylmethyl; $R^4$ is phthalidyl, or a 2,5-dihydro- 2-oxofuran-5-yl, 2-oxotetrahydrofuran-5-yl or 2-oxotetrahydrofuran-3-yl derivative unsubstituted or mono- or di-substituted by one or two groups selected from alkyl of 1 to 6 carbon atoms, alkoxy of 1 to 6 carbon atoms and phenyl; and X is sulphur.

5. A compound of formula (Ia) or a pharmaceutically acceptable salt or pharmaceutically acceptable in vivo hydrolysable ester thereof:

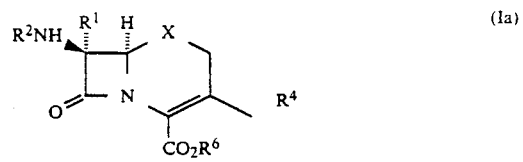

wherein $R^1$, $R^2$, $R^4$, X and the dashed line adjacent to $R^4$ are as defined with respect to formula (I) in claim 1 and $CO_2R^6$ is a carboxy group or a carboxylate anion.

6. A compound or a pharmaceutically acceptable salt or in vivo hydrolysable ester thereof according to claim 5, wherein the compound is selected from the group consisting of:

7β-[2-(2-aminothiazol-4-yl)-2-Z-methoxyimioacetamido]-3-(E-2,5-dihydro-3-methyl-2-oxofuran-5-ylidenemethyl)ceph-3-em-4-carboxylic acid, 7β-[2-(2-aminothiazol-4-yl)-2-Z-methoxyiminoacetamido]-3-[(5RS)-2,5-dihydro-2-oxofuran-5-yl-methyl]ceph-3-em-4-carboxylic acid, 7β-[2-(2-aminothiazol-4-yl)-2-Z-methoxyimioacetamido]-3-(E-phthalidhylidenemethyl)ceph-3-em-4-carboxylic acid, 7β-[2-(2-aminothiazol-4-yl)-2-Z-methoxyiminoacetamido]-3-(E-2,5-dihydro-4-methyl-2-oxo-3-phenylfuran-5-ylidenemethyl)ceph-3-em-4-carboxylic acid, 7β-[2-(2-aminothiazol-4-yl)-2-Z-hydroxyiminoacetamido]-3-(E-2,5-dihydro-3-methyl-2-oxofuran-5-ylidenemethyl)ceph-3-em-4-carboxylic acid, 7β-[2-(2-aminothiazol-4-yl)-2-Z-methoxyiminoacetamido]-3-(E-2,5-dihydro-4-methoxy-3-methyl-2-oxofuran-5-ylidenemethyl)ceph-3-em-4-carboxylic acid, 7β-[2-(2-aminothiazol-4-yl)-2-Z-methoxyiminoacetamido]-3-(Z-2,5-dihydro-4-methoxy-3-methyl-2-oxofuran-5-ylidenemethyl)ceph-3-em-4-carboxylic acid, 7β-[2-(2-aminothiazol-4-yl)-2-Z-methox-yiminoacetamido]-3-[(5RS)-2-oxotetrahydrofuran-5-ylmethyl]ceph-3-em-4-carboxylic acid, 7β-[2-(2-aminothiazol-4-yl)-2-Z-hydrox-yiminoacetamido]-3-(Z-2,5-dihydro-4-methoxy-3-methyl-2-oxofuran-5-ylidenemethyl)ceph-3-em-4-carboxylic acid, 7β-[2-(2-aminothiazol-4-yl)-2-Z-hydrox-yiminoacetamido]-3-(2,5-dihydro-2-oxofuran-5-ylmethyl)ceph-3-em-4-carboxylic acid, and 7β-[2-(2-aminothiazol-4-yl)-2-Z-methox-yiminoacetamido]-3-(2-oxotetrahydrofuran-3-ylidenemethyl)ceph-3-em-4-carboxylic acid.

7. A compound according to claim 2 wherein the 3-aryl-5-methylisoxazolyl is 3-(2-chloro-6-fluorophenyl)5-methoxylisoxazol-4-yl.

8. A pharmaceutical composition useful for treating bacterial infections in humans and animals which comprises an antibacterially effective amount of a compound of the formula (I):

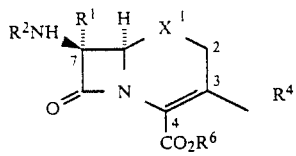

wherein
R$^1$ is hydrogen, methoxy or formamido;
R$^2$ is acyl;
CO$_2$R$^3$ is carboxy or a carboxylate anion, or R$^3$ is a readily removable carboxy protecting group; R$^4$ is a butenolide or butanolide ring, unsubstituted or substituted by one or two moieties selected from the group consisting of alkyl of 1 to 6 carbon atoms, dialkylamino of 1 to 6 carbon atoms in each alkyl moiety, alkoxy of 1 to 6 carbon atoms, hydroxy, halogen and aryl, wherein the aryl moiety is phenyl or naphthyl, unsubstituted or substituted with up to five substituents selected from the group consisting of halogen, mercapto, alkyl of 1 to 6 carbon atoms, phenyl, alkoxy of 1 to 6 carbon atoms, hydroxyalkyl of 1 to 6 carbon atoms, mercaptoalkyl of 1 to 6 carbon atoms, haloalkyl of 1 to 6 carbon atoms, hydroxy, amino, nitro, carboxy, alkylcarbonyloxy of 1 to 6 carbon atoms in the alkyl moiety, alkoxycarbonyl of 1 to 6 carbon atoms in the alkoxy moiety, formyl and alkylcarbonyl of 1 to 6 carbon atoms in the alkyl moiety, which may be the same or different, or, wherein two adjacent carbon atoms which are available for substitution define the common bond of phthalidyl unsubstituted or mono- or di- substituted with one or two substituents selected from the group consisting of alkyl of 1 to 6 carbon atoms, alkoxy of 1 to 6 carbon atoms, phenyl and naphthyl, said phenyl or naphthyl being unsubstituted or substituted with up to five substituents selected from the group consisting of halogen, mercapto, alkyl of 1 to 6 carbon atoms, phenyl, alkoxy of 1 to 6 carbon atoms, hydroxyalkyl of 1 to 6 carbon atoms, mercaptoalkyl of 1 to 6 carbon atoms, haloalkyl of 1 to 6 carbon atoms, hydroxy, amino, nitro, carboxy, alkylcarbonyloxy of 1 to 6 carbon atoms in the alkyl moiety, alkoxycarbonyl of 1 to 6 carbon atoms in the alkoxy moiety, formyl and alkylcarbonyl of 1 to 6 carbon atoms in the alkyl moiety;

X is S, SO or SO$_2$; and the dashed line adjacent to R$^4$ is an optional double bond, in combination with a pharmaceutically acceptable carrier.

9. A pharmaceutical composition according to claim 8 in which R$^2$ is acyl of the formula (a) to (f):

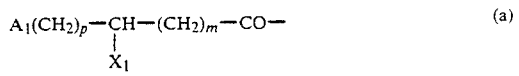

wherein p is 0, 1 or 2; m is 0, 1 or 2; A$_1$ is unsubstituted or substituted alkyl of 1 to 6 carbon atoms, cycloalkyl of 3 to 6 carbon atoms, cyclohexenyl, cyclohexadienyl, aromatic phenyl unsubstituted or substituted by phenyl, thienyl, pyridyl, or unsubstituted or substituted by up to three substituents selected from the group consisting of halogen, alkyl of 1 to 6 carbon atoms, alkoxy of 1 to 6 carbon atoms, haloalkyl of 1 to 6 carbon atoms, hydroxy and carboxy or a pharmaceutically acceptable salt or in vivo hydrolysable ester thereof, phenyl, naphthyl and oxo, alkylthio of 1 to 6 carbon atoms, or alkyloxy of 1 to 6 carbon atoms; X$_1$ is hydrogen, halogen, carboxylic acid or an in vivo hydrolysable ester thereof, sulphonic acid, azido, tetrazolyl, hydroxy, acyloxy, amino, ureido, acylamino wherein the acyl is selected from the group consisting of alkanoyl of 1 to 6 carbon atoms, benzoyl, trichloroethoxycarbonyl and chloroacetyl, heterocyclylamino of 4- to 7-ring members having up to four hetero-atoms in each ring selected from the group consisting of oxygen, nitrogen and sulphur, unsubstituted or substituted by up to three substituents selected from the group consisting of halogen, alkyl of 1 to 6 carbon atoms, alkoxy of 1 to 6 carbon atoms, haloalkyl of 1 to 6 carbon atoms, hydroxy, carboxy, pharmaceutically acceptable salts and in vivo hydrolysable esters, quanidino or acrylureido wherein the acyl is selected from the group consisting of alkanoyl of 1 to 6 carbon atoms, benzoyl, trichloroethoxycarbonyl and chloroacetyl; A$_2$ is phenyl, 2,6-dimethoxyphenyl,2-alkoxy-1-naphthyl, 3-arylisoxazoly, or 3-aryl-5-methylisoxazolyl wherein the aryl moiety is phenyl or naphthyl, unsubstituted or substituted with up to five substituents selected from the group consisting of halogen, mercapto, alkyl of 1 to 6 carbon atoms, phenyl, alkoxy of 1 to 6 carbon atoms, hydroxyalkyl of 1 to 6 carbon atoms, mercaptoalkyl of 1 to 6 carbon atoms, haloalkyl of 1 to 6 carbon atoms, hydroxy, amino, nitro, carboxy, alkylcarbonyloxy of 1 to 6 carbon atoms in the alkyl moiety, alkoxycarbonyl of 1 to 6 carbon atoms in the alkoxy moiety, formyl and alkylcarbonyl of 1 to 6 carbon atoms in the alkyl moiety is unsubstituted or substituted phenyl or naphthyl; substituted alkyl of 1 to 6 carbon atoms; or dithietane substituted by up to three substituents selected from the group consisting of halogen, alkyl of 1 to 6 carbon atoms, alkoxy of 1 to 6 carbon atoms, haloalkyl of 1 to 6 carbon atoms, hydroxy and carboxy or a pharmaceutically acceptable salt or in vivo hydrolysable ester thereof, phenyl, naphthyl and oxo; $X_2$ is $CH_2OCH_2$, $CH_2SCH_2$ or alkylene; $X_3$ is oxygen or sulphur; $A_3$ is unsubstituted or substituted phenyl or aminothiazolyl in which the amino group is protected or not protected; and $A_4$ is hydrogen, alkyl of 1 to 6 carbon atoms, cycloalkyl of 3 to 8 carbon atoms, alkoxycarbonyl alkyl of 1 to 6 carbon atoms in each alkyl moiety, alkenyl of 2 to 6 carbon atoms, carboxy alkyl of 1 to 6 carbon atoms, alkylnyl of 2 to 6 carbon atoms, aryl and aryl alkyl of 1 to 6 carbon atoms, wherein the aryl moiety is phenyl or naphthyl, unsubstituted or substituted with up to five substituents selected from the group consisting of halogen, mercapto, alkyl of 1 to 6 carbon atoms, phenyl, alkoxy of 1 to 6 carbon atoms, hydroxyalkyl of 1 to 6 carbon atoms, mercaptoalkyl of 1 to 6 carbon atoms, haloalkyl of 1 to 6 carbon atoms, hydroxy, amino, nitro, carboxy, alkylcarbonyloxy of 1 to 6 carbon atoms in the alkyl moiety, alkoxycarbonyl of 1 to 6 carbon atoms in the alkoxy moiety, formyl and alkylcarbonyl of 1 to 6 carbon atoms in the alkyl moiety wherein the substituents for phenyl or naphthyl are up to 5 substituents selected from the group consisting of halogen, mercapto, alkyl of 1 to 6 carbon atoms, phenyl, alkoxy of 1 to 6 carbon atoms, hydroxyalkyl of 1 to 6 carbon atoms, mercaptoalkyl of 1 to 6 carbon atoms, haloalkyl of 1 to 6 carbon atoms, hydroxy, amino, nitro, carboxy, alkylcarbonyloxy of 1 to 6 carbon atoms in the alkyl moiety, alkoxycarbonyl of 1 to 6 carbon atoms in the alkyl moiety, formyl and alkylcarbonyl of 1 to 6 carbon atoms in the alkyl moiety.

10. A pharmaceutical composition according to claim 8, in which $R^2$ is acyl of the formula (a) wherein $A_1$ is phenyl, $X_1$ is hydrogen and p and m are 0; or $R^2$ is acyl of the formula (e) wherein $A_3$ is 2-aminothiazol-4-yl or 2-tritylaminothiazol-4-yl and $A_4$ is hydrogen, methyl, or triphenylmethyl.

11. A pharmaceutical composition according to claim 8, wherein the compound is of the formula (Ia):

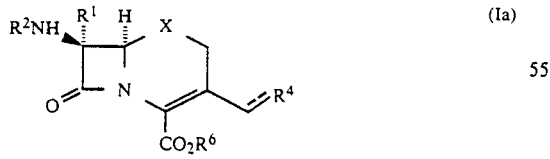

(Ia)

or a pharmaceutically acceptable salt or pharmaceutically acceptable in vivo hydrolyzable ester thereof, wherein R, $R^1$, $R^4$, X and the dashed line adjacent to $R^4$ are as defined with respect to formula (I) in claim 8 and $CO_2R^6$ is carboxy or a carboxylate anion.

12. A pharmaceutical composition according to claim 11, wherein the compound is selected from the group consisting of:

7β-[2-(2-aminothiazol-4-yl)-2-Z-methoxyiminoacetamido]-3-(3-2,5-dihydro-3-methyl-2-oxofuran-5-ylidenemethyl)ceph-3-em-4-carboxylic acid, 7β-[2-(2-aminothiazol-4-yl)-2-Z-methoxyiminoacetamido]-3-[(5RS)-2,5-dihydro-2-oxofuran-5-yl-methyl]ceph-3-em-4-carboxylic acid, 6β-[2-(2-aminothiazol-4-yl)-2-Z-methoxyiminoacetamido]-3-(E-phthalidhylidenemethyl)-ceph-3-em-4-carboxylic acid, 7β-[2-(2-aminothiazol-4-yl)-2-Z-methoxyiminoacetamido]-3-(E-2,5-dihydro-4-methyl-2-oxo-3-phenylfuran-5-ylidenemethyl)ceph-3-em-4-carboxylic acid, 7β-[2-(2-aminothiazol-4-yl)-2-Z-hydroxyiminoacetamido]-3-(E-2,5-dihydro-3-methyl-2-oxofuran-5-ylidenemethyl)ceph-3-em-4carboxylic acid, 7β-[2-(2-aminothiazol-4-yl)-2-Z-methoxyiminoacetamido]-3-(E-2,5-dihydro-4-methoxy-3-methyl-2-oxofuran-5-ylidenemethyl)ceph-3-em-4-carboxylic acid, 7β-[2-(2-aminothiazol-4-yl)-2-Z-methoxyiminoacetamido]-3-(Z-2,5-dihydro-4-methoxy-3-methyl-2-oxofuran-5-ylidenemethyl)ceph-3-em-4-carboxylic acid, 7β-[2-(2-aminothiazol-4yl)-2-Z-methoxyiminoacetamido]-3-[(5RS)-2-oxotetrahydrofuran-5-ylmethyl]ceph-3-em-4-carboxylic acid, 7β-[2-(2-aminothiazol-4-yl)-2-Z-hydroxyiminoacetamido]-3-(Z-2,5-dihydro-4-methoxy-3-methyl-2-oxofuran-5-ylidenemethyl)ceph-3-em-4-carboxylic acid, 7β-[2-(2-aminothiazol-4-yl)-2-Z-hydroxyiminoacetamido]-3-(2,5-dihydro-2-oxofuran-5-ylmethyl)ceph-3-em-4-carboxylic acid, and 7β-[2-(2-aminothiazol-4-yl)-2-Z-methoxyiminoacetamido]-3-(2-oxotetrahydrofuran-3-yldienemethyl)ceph-3-em-4-carboxylic acid or a pharmaceutically acceptable salt or pharmaceutically acceptable in vivo hydrolyzable ester thereof.

13. A pharmaceutical composition according to claim 8, which comprises a β-lactamase inhibitory amount of a β-lactamase inhibitor.

14. A pharmaceutical composition according to claim 9, wherein the 3-aryl-5-methylisoxazolyl is 3-(2-chlor-6-fluorophenyl)5-methylisoxazol-4-yl.

15. A method of treating bacterial infections in humans and animals which comprises the administering to a human or animal in need thereof an antibacterially effective amount of a compound of formula (I):

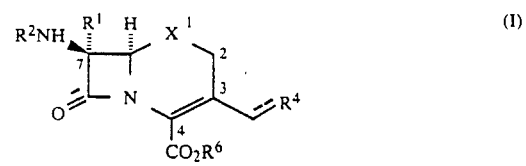

(I)

wherein
$R^1$ is hydrogen, methoxy or formamido;
$R^2$ is acyl;
$CO_2R^3$ is carboxy or a carboxylate anion, or $R^3$ is a readily removable carboxy protecting group; $R^4$ is a butenolide or butanolide ring, unsubstituted or substituted by one or two moieties selected from the group consisting of alkyl of 1 to 6 carbon atoms, dialkylamino of 1 to 6 carbon atoms in each alkyl moiety, alkoxy of 1 to 6 carbon atoms, hydroxy, halogen and aryl, wherein the aryl moiety is phenyl or naphthyl, unsubstituted or substituted with up to five substituents selected from the group consisting of halogen, mercapto, alkyl of 1 to 6 carbon atoms, phenyl, alkoxy of 1 to 6 carbon atoms, hydroxyalkyl of 1 to 6 carbon atoms, mercaptoalkyl of 1 to 6 carbon atoms, haloalkyl of 1 to 6 carbon atoms, hydroxy, amino, nitro, carboxy, alkylcarbonyl of 1 to 6 carbon atoms in the alkoxy moiety, alkoxycarbonyl of 1 to 6 carbon atoms in the alkoxy moiety, formyl and alkylcarbonyl of 1 to 6 carbon atoms in the alkyl moiety, which may be the same or different, or, wherein two adjacent carbon atoms which are available for substitution define the common bond of phthalidyl unsubstituted or mono- or di- substituted with one or two substituents selected from the group consisting of alkyl of 1 to 6 carbon atoms, alkoxy of 1 to 6 carbon atoms, phenyl and naphthyl, said phenyl or naphthyl being unsubstituted or substituted with up to five substituents selected from the group consisting of halogen, mercapto, alkyl of 1 to 6 carbon atoms, phenyl, alkoxy of 1 to 6 carbon atoms, hydroxyalkyl of 1 to 6 carbon atoms, mercaptoalkyl of 1 to 6 carbon atoms, haloalkyl of 1 to 6 carbon atoms, hydroxy, amino, nitro, carboxy, alkylcarbonyloxy of 1 to 6 carbon atoms in the alkyl moiety, alkoxycarbonyl of 1 to 6 carbon atoms in the alkoxy moiety, formyl and alkylcarbonyl of 1 to 6 carbon atoms in the alkyl moiety;

X is S, SO or $SO_2$; and the dashed line adjacent to $R^4$ is an optional double bond in combination with a pharmaceutically acceptable carrier.

16. A method according to claim 15 in which $R^1$ is an acyl of the formula (a) to (f):

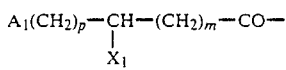  (a)

$A_2CO-$  (b)

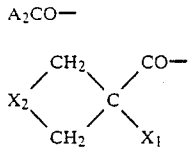  (c)

$A_2-X_3-(CH_2)_p-CO-$  (d)

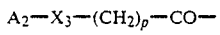  (e)

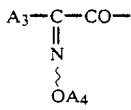

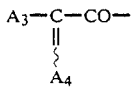  (f)

wherein p is 0, 1 or 2; m is 0, 1 or 2; $A_1$ is unsubstituted or substituted alkyl of 1 to 6 carbon atoms, cycloalkyl of 3 to 6 carbon atoms, cyclohexenyl, cyclohexadienyl, phenyl unsubstituted or substituted by phenyl, thienyl, pyridyl, or thiazolyl unsubstituted or substituted by up to three substituents selected from the group consisting of halogen, alkyl of 1 to 6 carbon atoms, alkoxy of 1 to 6carbon atoms, haloalkyl of 1 to 6 carbon atoms, hydroxy and carboxy or a pharmaceutically acceptable salt or in vivo hydrolysable ester thereof, phenyl, naphthyl and oxo, alkylthio of 1 to 6 carbon atoms or alkyloxy of 1 to 6 carbon atoms; $X_1$ is hydrogen, halogen, carboxylic acid or an in vivo hydrolysable ester thereof, sulphonic acid, azido, tetrazolyl, hydroxy, acyloxy, amino, ureido, acylamino wherein the acyl is selected from the group consisting of alkanoyl of 1 to 6 carbon atoms, benzoyl, trichloroethoxycarbonyl and chloroacetyl, heterocyclylamino of 4- to 7- ring members having up to four hetero-atoms in each ring selected from the group consisting of oxygen, nitrogen and sulphur, unsubstituted or substituted by up to three substituents selected from the group consisting of halogen, alkyl of 1 to 6 carbon atoms, alkoxy of 1 to 6 carbon atoms, haloalkyl of 1 to 6 carbon atoms, hydroxy, carboxy, pharmaceutically acceptable salts and in vivo hydrolysable esters, guanidino or acylureido wherein the aryl is selected from the group consisting of alkanoyl of 1 to 6 carbon atoms, benzoyl, trichloroethoxycarbonyl and chloroacetyl; $A_2$ is phenyl, 2,6-dimethoxyphenyl,2-alkoxy-1-naphthyl, 3-arylisoxazolyl, or 3-aryl-5-methylisoxazolyl wherein the aryl moiety is phenyl or naphthyl, unsubstituted or substituted with up to five substituents selected from the group consisting of halogen, mercapto, alkyl of 1 to 6 carbon atoms, phenyl, alkoxy of 1 to 6 carbon atoms, hydroxyalkyl of 1 to 6 carbon atoms, mercaptoalkyl of 1 to 6 carbon atoms, haloalkyl of 1 to 6 carbon atoms, hydroxy, amino, nitro, carboxy, alkylcarbonyloxy of 1 to 6 carbon atoms in the alkyl moiety, alkoxycarbonyl of 1 to 6 carbon atoms in the alkoxy moiety, formyl and alkylcarbonyl of 1 to 6 carbon atoms i the alkyl moiety is unsubstituted or substituted phenyl or naphthyl; substituted alkyl of 1 to 6 carbon atoms; or dithietane substituted by up to three substituents selected from the group consisting of halogen, alkyl of 1 to 6 carbon atoms, alkoxy of 1 to 6 carbon atoms, haloalkyl of 1 to 6 carbon atoms, hydroxy and carboxy or a pharmaceutically acceptable salt or in vivo hydrolysable ester thereof, phenyl, naphthyl and oxo; $X_2$ is $CH_2OCH_2$, $CH_2SCH_2$ or alkylene; $X_3$ is oxygen or sulphur; $A_3$ is unsubstituted or substituted phenyl or aminothiazolyl in which the amino group is protected or not protected; and $A_4$ is hydrogen, alkyl of 1 to 6 carbon atoms, cycloalkyl of 3 to 8 carbon atoms, alkoxycarbonylalkyl of 1 to 6 carbon atoms in each alkyl moiety, alkenyl of 2 to 6 carbon atoms, carboxyalkyl of 1 to 6 carbon atoms, alkynyl of 2 to 6 carbon atoms, aryl and arylalkyl of 1 to 6 carbon atoms, wherein the aryl moiety is phenyl or naphthyl, unsubstituted or substituted with up to five substituents selected from the group consisting of halogen, mercapto, alkyl of 1 to 6 carbon atoms, phenyl, alkoxy of 1 to b 6 carbon atoms, hydroxyalkyl of 1 to 6 carbon atoms, mercaptalkyl of 1 to 6 carbon atoms, haloalkyl of 1 to 6 carbon atoms, hydroxy, amino, nitro, carboxy, alkylcarbonyloxy of 1 to 6 carbon atoms in the alkyl moiety, alkoxycarbonyl of 1 to 6 carbon atoms in the alkoxy moiety, formyl and alkylcarbonyl of 1 to 6 carbon atoms in the alkyl moiety wherein the substituents for phenyl or naphthyl are up to 5 substituents selected from the group consisting of halogen, mercapto, alkyl of 1 to 6 carbon atoms, phenyl, alkoxy of 1 to 6 carbon atoms, hydroxylalkyl of 1 to 6 carbon atoms, mercaptoalkyl of 1 to 6 carbon atoms, haloalkyl of 1 to 6 carbon atoms, hydroxy, amino, nitro, carboxy, alkylcarbonyloxy of 1 to 6 carbon atoms in the alkyl moiety, alkoxycarbonyl of 1 to 6 carbon atoms, formyl and alkylcarbonyl of 1 to 6 carbon atoms in the alkyl moiety.

17. A method according to claim 15, in which $R^2$ is acyl of the formula (a) wherein $A_1$ is phenyl, $X_1$ is hydrogen and p and m are O; or $R^2$ is acyl of the formula (e) wherein $A_3$ is 2-aminothiazol-4-yl or 2-tritylaminothiazol-4-yl and $A_4$ is hydrogen, methyl, or triphenylmethyl.

18. A method according to claim 13, wherein the compound is of the formula (Ia):

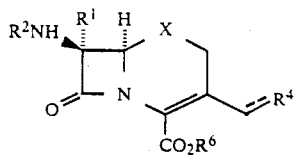

or a pharmaceutically acceptable salt or pharmaceutically acceptable in vivo hydrolyzable ester thereof, wherein R, $R^1$, $R^4$, X and the dashed line adjacent to $R^4$ are as defined with respect to formula (I) in claim 8 and $CO_2R^6$ is carboxy or a carboxylate anion.

19. A method according to claim 18, wherein the compound is selected from the group consisting of:

7β-[2-(2-aminothiazol-4-yl)-2-Z-methoxyiminoacetamido]-3-(E-2,5-dihydro-3-methyl-2-oxofuran-5-ylidenemethyl)ceph-3-em-4-carboxylic acid, 7β-[2-(2-aminothiazol-4-yl)-2-Z-methoxyiminoacetamido]-3-[(5RS)-2,5-dihydro-2-oxofuran-5-yl-methyl]ceph-3-em-4-carboxylic acid, 7β-[2-(2-aminothiazol-4-yl)-2-Z-methoxyiminoacetamido]-3-(E-phthalidhylidenemethyl)-ceph-3-em-4-carboxylic acid, 7β-[2-(2-aminothiazol-4-yl)-2-Z-methoxyiminoacetamido]-3-(E-2,5-dihydro-4-methyl-2-oxo-3-phenylfuran-5-ylidenemethyl)ceph-3-em-4-carboxylic acid, 7β-[2-(2-aminothiazol-4-yl)-2-Z-hydroxyiminoacetamido]-3-(E-2,5-dihydro-3-methyl-2-oxofuran-5-ylidenemethyl)ceph-3-em-4-carboxylic acid, 7β-[2-(2-aminothiazol-4-yl)-2-methoxyiminoacetamido]-3-(E-2,5-dihydro-4-methoxy-3-methyl-2-oxofuran-5-ylidenemethyl)ceph-3-em-4-carboxylic acid, 7β-[2-(2-aminothiazol-4-yl)-2-Z-methoxyiminoacetamido]-3-(Z-2,5-dihydro-4-methoxy-3-methoxy-2-oxofuran-5-ylidenemethyl)ceph-3-em-4-carboxylic acid, 7β-[2-(2-aminothiazol-4-yl)-2-Z-methoxyiminoacetamido]-3-[(5RS)-2-oxotetrahydrofuran-5-ylmethyl]ceph-3-em-4-carboxylic acid, 7β-[2-(2-aminothiazol-4-yl)-2-Z-hydroxyiminoacetamido]-3-(Z-2,5-dihydro-4-methoxy-3-methyl-2-oxofuran-5-ylidenemethyl)ceph-3-em-4-carboxylic acid, 7β-[2-(2-aminothiazol-4-yl)-2-Z-hydroxyiminoacetamido]-3-(2,5-dihydro-2-oxofuran-5-ylmethyl)ceph-3-em-4-carboxylic acid, and 7β-[2-(2-aminothiazol-4-yl)-2-Z-methoxyiminoacetamido]-3-(2-oxotetrahydrofuran-3-ylidenemethyl)ceph-3-em-4-carboxylic acid or a pharmaceutically acceptable salt or pharmaceutically acceptable in vivo hydrolyzable ester thereof.

20. A method according to claim 15 which comprises administering a β-lactamase inhibitory amount of a β-lactamase inhibitor and said compound of formula I.

21. A method according to claim 16, wherein the 3-aryl-5-methylisoxazolyl is 3-(2-chloro-6-fluorophenyl)5-methylisoxazol-4-yl.

* * * * *